United States Patent
James et al.

(10) Patent No.: US 7,695,930 B2
(45) Date of Patent: Apr. 13, 2010

(54) METHOD FOR THE DETECTION, IDENTIFICATION AND/OR QUANTIFICATION OF MICROOGANISMS WITH PEPTIDASE ACTIVITY USING PHENOXAZINONE DERIVATIVES AS ENZYME SUBSTRATES

(75) Inventors: Arthur James, Cockermouth (GB); John Perry, Newcastle-Upon-Tyne (GB); Annette Rigby, Haltwhistle (GB); Stephen Stanforth, Stocksfield (GB)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 12/219,422

(22) Filed: Jul. 22, 2008

(65) Prior Publication Data

US 2008/0286820 A1    Nov. 20, 2008

Related U.S. Application Data

(62) Division of application No. 10/554,461, filed as application No. PCT/FR2004/050193 on May 13, 2004, now Pat. No. 7,420,054.

(30) Foreign Application Priority Data

May 13, 2003    (FR) .................................... 03 05719

(51) Int. Cl.
    *C12Q 1/37*    (2006.01)
(52) U.S. Cl. .............................. 435/24; 435/23; 544/99; 544/102
(58) Field of Classification Search .................. 435/24, 435/23; 544/99, 102
    See application file for complete search history.

(56) References Cited

U.S. PATENT DOCUMENTS

| | | | |
|---|---|---|---|
| 5,336,600 A | 8/1994 | Monget | |
| 6,235,493 B1 | 5/2001 | Bissell et al. | |
| 7,420,054 B2 * | 9/2008 | James et al. | ............... 544/99 |

FOREIGN PATENT DOCUMENTS

| | | |
|---|---|---|
| EP | 0 156 347 A2 | 10/1985 |
| EP | 0 656 421 A1 | 6/1995 |
| JP | A-04-506753 | 11/1992 |
| JP | A-05-30995 | 2/1993 |
| JP | A-2001-061495 | 3/2001 |
| JP | A-2002-10799 | 1/2002 |
| WO | WO 91/14787 A1 | 10/1991 |
| WO | WO 98/04735 | 2/1998 |
| WO | WO 99/09207 | 2/1999 |
| WO | WO 99/38995 | 8/1999 |
| WO | WO 01/42491 A2 | 6/2001 |

OTHER PUBLICATIONS

Nakanishi et al., "Imaging of Conformational Changes of Proteins with a New Environment-Sensitive Fluorescent Probe Designed for Site-Specific Labeling of Recombinant Proteins in Live Cells," Analytical Chemistry, vol. 73, No. 13, Jul. 1, 2001.

Stuzka et al., "Oxazine ALS Zaidobasische Indikatoren I," Collection Czech. Chem Commun., 28, pp. 1399-1407, 1963.

Japanese Office Action for corresponding Japanese Patent Application No. 2006-530437 dated Nov. 17, 2009 (with English translation).

* cited by examiner

*Primary Examiner*—Ralph Gitomer
(74) *Attorney, Agent, or Firm*—Oliff & Berridge, PLC

(57) ABSTRACT

The present invention relates to methods for the detection, identification and/or quantification of microorganisms with peptidase activity using enzymatic substrates with the following general formula:

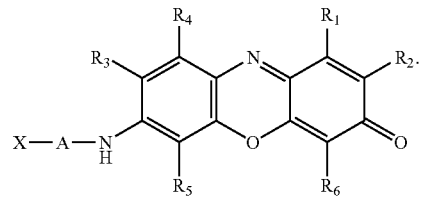

12 Claims, No Drawings

METHOD FOR THE DETECTION, IDENTIFICATION AND/OR QUANTIFICATION OF MICROOGANISMS WITH PEPTIDASE ACTIVITY USING PHENOXAZINONE DERIVATIVES AS ENZYME SUBSTRATES

This is a Division of application Ser. No. 10/554,461 filed Oct. 25, 2005 now U.S. Pat. 7,420,054, which is a National Phase of Application No. PCT/FR2004/050193 filed May 13, 2004, which claims the benefit of French Application No. 0305719 filed May 13, 2003. The disclosure of the prior applications is hereby incorporated by reference herein in their entirety.

The present invention relates to novel chromogenic enzymatic substrates for detecting peptidase activity. These substrates can be used in applications comprising an enzymatic hydrolysis step that produces a physicochemical signal, in particular in microbiology, biochemistry, immunology, molecular biology, histology, etc. Compared with existing substrates, most of which are fluorigenic, the chromogenic substrates of the invention can be used in particular in a gelled medium for detecting microorganisms since they produce a coloration that does not diffuse in the reaction medium and is therefore concentrated in the colonies.

The invention also relates to reaction media containing such substrates, to the use of the substrates or of the media for detecting Gram-negative bacteria, Gram-positive bacteria and yeast expressing peptidase activity, and to methods of use.

The name aminopeptidase is generally give to an enzyme capable of cleaving, by hydrolysis, the amide group formed between an acyl of an amino acid and a primary amine, and the name peptidase is given to an enzyme capable of cleaving, by hydrolysis, the amide group formed between the acyl residue of a peptide and a primary amine. In the present application, the term "peptidase" can denote, as appropriate, both a peptidase and an aminopeptidase as defined above.

Chromogenic enzymatic substrates for detecting peptidase activity that do not diffuse are described and already known from the state of the art. Thus, such substrates are covered by patent applications WO-A-98/04735 and WO-A-99/38995 filed by the applicant. However, these substrates exhibit various drawbacks: they are difficult to synthesize, the purity is low and the yields are low. In addition, for use in culture media, it is necessary to define a medium composition that is very precise in order to observe a color. None of the other substrates currently described can be used in solid media for detecting microorganisms in mixed cultures.

Molecules derived from phenoxazione are known for their ability to produce fluorescence. They can be used:
- as acid-base indicators, as described for example in Stuzka, V. et al., 1963, Collection Czech. Chem. Commun., 28, 1399-1407, or else
- as fluorescent labels, for example for following conformational modifications of proteins, as described in Nakanishi J. et al., 2001, Analytical Chemistry, 73(13), 2920-2928.

No phenoxazinone derivative has ever been used as an enzymatic substrate.

In accordance with the present invention, novel chromogenic enzymatic substrates for detecting microorganisms expressing peptidase activity are proposed. The invention also relates to reaction media containing such substrates, and also to the use of the substrates or of the media for detecting peptidase activities, and to methods of use.

In fact, the applicant has found, surprisingly, that it is possible to detect microorganisms expressing peptidase activity by using chromogenic phenoxazinone derivatives that produce a coloration that does not diffuse in the reaction medium, and is therefore concentrated in the colonies, the peptidase activity being demonstrated by a modification of the coloration of the colonies in the culture medium.

After seeding of the reaction media containing the substrates of the invention with the microorganisms to be tested, colonies that are colorless to white are observed when the latter are not capable of hydrolyzing the substrate. On the other hand, colored colonies are observed when they are capable of hydrolyzing the substrate of the invention.

The phenoxazinone derivatives of the invention are both chromogenic and fluorigenic and have the advantage of good detection sensitivity.

Thus, a subject of the present invention is chromogenic enzymatic substrates of formula (I):

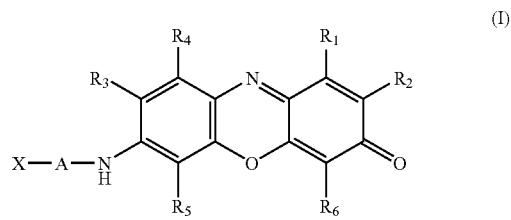

in which
$R_1$ and $R_2$ form, with the phenyl ring to which they are attached, a naphthalene ring of formula:

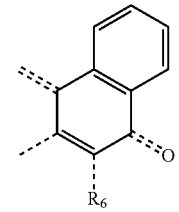

or an optionally substituted coumarin ring of formula:

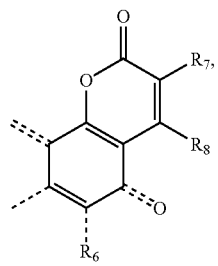

or else $R_1$ and $R_2$ each independently represent a hydrogen atom, a $C_1$-$C_6$ alkyl group, a halogen atom, a —C(O)OR' group, a C(O)NR'R" group, an —SO$_3$H group or a sulfonamide group, $R_3$ and $R_4$ form, with the phenyl ring to which they are attached, an optionally substituted naphthalene ring of formula:

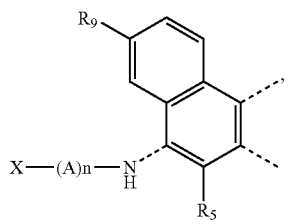

or else $R_3$ and $R_4$ each independently represent a hydrogen atom, a halogen atom, a —C(O)OR' group, a C(O)NR'R" group, an —SO$_3$H group or a sulfonamide group, it being understood that:
(i) at least one among $R_1/R_2$ and $R_3/R_4$ forms, with the phenyl ring to which it is attached, an optionally substituted naphthalene or coumarin ring as defined above, and
(ii) when $R_1$ and $R_2$ form, with the phenyl ring to which they are attached, an optionally substituted coumarin ring, $R_3$ and $R_4$ do not form, with the phenyl ring to which they are attached, an optionally substituted naphthalene ring, $R_5$ and $R_6$ each independently represent a hydrogen atom, a halogen atom, a —C(O)OR' group, a C(O)NR'R" group, or a $C_1$-$C_6$ alkyl group, it being understood that $R_6$ represents a halogen atom when $R_1/R_2$ and $R_3/R_4$ each form, with the phenyl ring to which they are attached, a naphthalene ring, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or else $R_7$ and $R_8$, together with the two carbon atoms to which they are attached, form a $C_4$-$C_6$ ring, $R_9$ represents a hydrogen atom, a bromine atom, a chlorine atom, a benzoyl group, a —CO$_2$H group or an —SO$_3$H group, it being understood that, when $R_9$ is different from a hydrogen atom, then $R_5$ is a hydrogen atom, R' represents a hydrogen atom or a $C_1$-$C_6$ alkyl group, R" represents a hydrogen atom or a $C_1$-$C_6$ alkyl group, or else R' and R", together with the nitrogen atom to which they are attached, form a heterocyclic ring containing one or more hetero atoms, A represents at least one amino acid, and X represents a blocking agent or nothing.

According to the invention, the term "aryl" is in particular intended to mean a $C_6$-$C_{10}$ aromatic ring, in particular phenyl, benzyl, 1-naphthyl or 2-naphthyl. The same is true for the aryl part of the aralkyl groups.

The alkyls according to the invention, in the aralkyl and carboxyalkyl groups, are also $C_1$-$C_6$.

The term "$C_1$-$C_6$ alkyl" is intended to mean a straight or branched alkyl having from 1 to 6 carbon atoms. By way of example, mention may be made of methyl, ethyl, propyl, isopropyl, butyl, t-butyl, pentyl, isopentyl and hexyl.

The term "halogen atom" is intended to mean chlorine, bromine, iodine and fluorine.

The term "hetero atom" is intended to mean an atom other than a carbon atom, such as O, N or S.

The heterocyclic rings that R' and R" can form may be of any size, but they preferably contain from 5 to 7 ring members.

Examples of a heterocyclic ring comprise the morpholine, piperazine, piperidine, pyrrolidine and imidazolidine ring.

The various naphthalene and coumarin rings formed by the substituents $R_1/R_2$ and $R_3/R_4$ according to the description of the invention are represented by including dashed lines completed with the corresponding substituents in the interests of clarity, and make it possible to visualize the position of said rings in the phenoxazinone derivatives of formula (I) of the invention.

The blocking agents according to the invention comprise any blocking agent known to those skilled in the art which is capable of protecting amines. By way of example, mention may be made of t-butoxycarbonyl (N-tBOC), 9-fluorenyloxycarbonyl, a solubilizing agent such as succinyl, or else a non-metabolizable, i.e. non-natural, amino acid such as pipecolic acid.

The blocking agents are not systematically present in the compounds of the invention. In this case, when the compounds of the invention do not have a blocking agent (X is nothing), the compounds of the invention are in the form of a salt such as chloride, bromide or trifluoroacetate.

The amino acids that are represented by A in formula (I) are any amino acid known to those skilled in the art.

According to one embodiment of the invention, A represents an amino acid or a peptide having at most 10 amino acids in which the amino acids are identical or different. Preferably, for reasons of substrate costs, A represents an amino acid or a peptide having at most 4 amino acids in which the amino acids are identical or different.

According to one embodiment, the compounds of the invention have the formula (I):

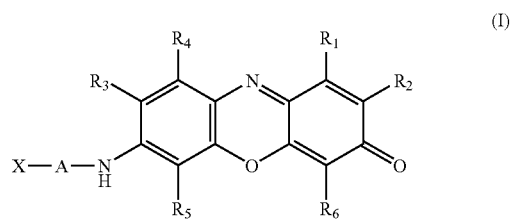

(I)

in which $R_1$ and $R_2$ form, with the phenyl ring to which they are attached, a naphthalene ring of formula:

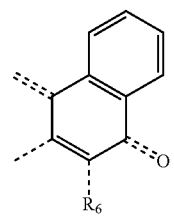

or an optionally substituted coumarin ring of formula:

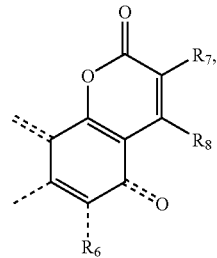

or else $R_1$ and $R_2$ each independently represent a hydrogen atom, a $C_1$-$C_6$ alkyl group, a halogen atom, a —C(O)OR' group, a C(O)NR'R" group, an —SO$_3$H group or a sulfonamide group, $R_3$ and $R_4$ form, with the phenyl ring to which they are attached, an optionally substituted naphthalene ring of formula:

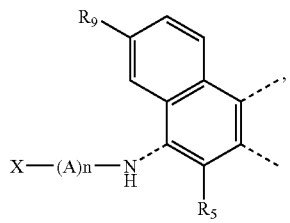

or else $R_3$ and $R_4$ each independently represent a hydrogen atom, a halogen atom, a —C(O)OR' group, a C(O)NR'R" group, an —SO$_3$H group or a sulfonamide group, it being understood that:
(i) at least one among $R_1$/$R_2$ and $R_3$/$R_4$ forms, with the phenyl ring to which it is attached, an optionally substituted naphthalene or coumarin ring as defined above, and
(ii) when $R_1$ and $R_2$ form, with the phenyl ring to which they are attached, an optionally substituted coumarin ring, $R_3$ and $R_4$ do not form, with the phenyl ring to which they are attached, an optionally substituted naphthalene ring, $R_5$ and $R_6$ each independently represent a hydrogen atom, a halogen atom, a —C(O)OR' group, a C(O)NR'R" group, or a $C_1$-$C_6$ alkyl group, it being understood that
(i) $R_6$ represents a hydrogen atom when $R_1$ and $R_2$ form, with the phenyl ring to which they are attached, a naphthalene or coumarin ring, and
(ii) $R_6$ represents a halogen atom when $R_1$/$R_2$ and $R_3$/$R_4$ each form, with the phenyl ring to which they are attached, a benzene ring, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or else $R_7$ and $R_8$, together with the two carbon atoms to which they are attached, form a $C_4$-$C_6$ ring, $R_9$ represents a hydrogen atom, a bromine atom, a chlorine atom, a benzoyl group, a —CO$_2$H group or an —SO$_3$H group, it being understood that, when $R_9$ is different from a hydrogen atom, then $R_5$ is a hydrogen atom, R' represents a hydrogen atom or a $C_1$-$C_6$ alkyl group,
R" represents a hydrogen atom or a $C_1$-$C_6$ alkyl group,
or else R' and R", together with the nitrogen atom to which they are attached, form a heterocyclic ring containing one or more hetero atoms, A represents at least one amino acid, and
X represents a blocking agent or nothing.

According to another embodiment, the compounds of the invention are chosen from the compounds of formula (I) in which $R_1$ and $R_2$ form, with the phenyl ring to which they are attached, a naphthalene ring, or else $R_1$ and $R_2$ form, with the phenyl ring to which they are attached, a coumarin ring, or else $R_3$ and $R_4$ form, with the phenyl ring to which they are attached, a naphthalene ring, the other substituents being as defined above, it being understood that, when $R_1$/$R_2$ forms a naphthalene or coumarin ring with the phenyl ring to which they are attached, $R_3$/$R_4$ do not at the same time form a naphthalene ring with the phenyl ring to which they are attached, and vice versa.

Thus, according to this embodiment, the enzymatic substrates are compounds of formula (I) below:

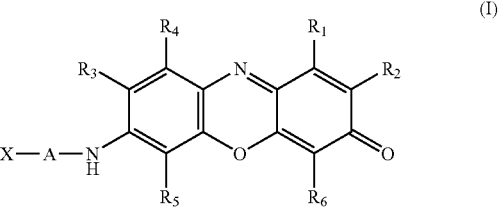

(I)

in which
$R_1$ and $R_2$ form, with the phenyl ring to which they are attached, a naphthalene ring of formula:

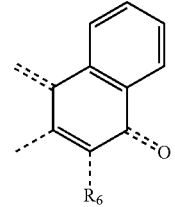

or an optionally substituted coumarin ring of formula:

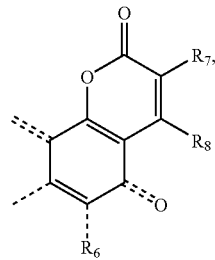

or else $R_1$ and $R_2$ each independently represent a hydrogen atom, a $C_1$-$C_6$ alkyl group, a halogen atom, a —C(O)OR' group, a C(O)NR'R" group, an —SO$_3$H group or a sulfonamide group, $R_3$ and $R_4$ form, with the phenyl ring to which they are attached, an optionally substituted naphthalene ring of formula:

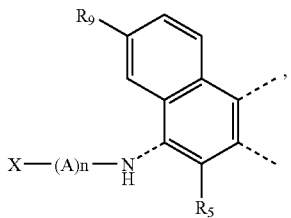

or else $R_3$ and $R_4$ each independently represent a hydrogen atom, a halogen atom, a —C(O)OR' group, a C(O)NR'R" group, an —SO$_3$H group or a sulfonamide group, it being understood that: one and only one among $R_1/R_2$ and $R_3/R_4$ forms, with the phenyl ring to which it is attached, an optionally substituted naphthalene or coumarin ring as defined above, $R_5$ and $R_6$ each independently represent a hydrogen atom, a halogen atom, a —C(O)OR' group, a C(O)NR'R" group, or a $C_1$-$C_6$ alkyl group, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or else $R_7$ and $R_8$, together with the two carbon atoms to which they are attached, form a $C_4$-$C_6$ ring, $R_9$ represents a hydrogen atom, a bromine atom, a chlorine atom, a benzoyl group, a —CO$_2$H group or an —SO$_3$H group, it being understood that, when $R_9$ is different from a hydrogen atom, then $R_5$ is a hydrogen atom, R' represents a hydrogen atom or a $C_1$-$C_6$ alkyl group, R" represents a hydrogen atom or a $C_1$-$C_6$ alkyl group, or else R' and R", together with the nitrogen atom to which they are attached, form a heterocyclic ring containing one or more hetero atoms, A represents at least one amino acid, and X represents a blocking agent or nothing.

According to one embodiment of the invention, A represents an amino acid or a peptide having at most 10 amino acids in which the amino acids are identical or different. Preferably, A represents an amino acid or a peptide having at most 4 amino acids in which the amino acids are identical or different.

According to a particular embodiment, the compounds of the invention are enzymatic substrates with the following formula (Ia):

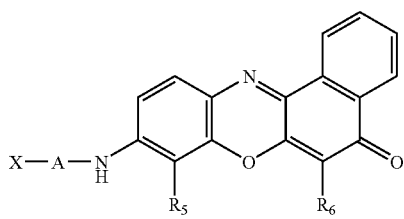

(Ia)

in which $R_5$, $R_6$ and A and X are as defined above.

The compounds of formula (Ia) are compounds of formula (I) in which the radicals $R_1$ and $R_2$ form, with the phenyl ring to which they are attached, a naphthalene ring and $R_3$ and $R_4$ are each a hydrogen atom.

Preferably, in the compounds of formula (Ia), $R_5$ represents a hydrogen atom, $R_6$ represents a hydrogen atom or a halogen atom, such as a chlorine atom, A is an amino acid chosen from leucine, proline and alanine, and X is the t-butoxycarbonyl blocking agent or nothing.

According to another particular embodiment, the compounds of the invention are enzymatic substrates of formula (Ib):

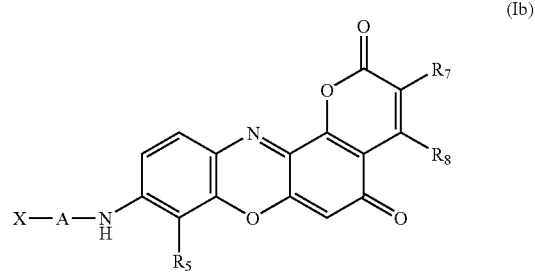

(Ib)

in which $R_5$, $R_7$, $R_8$, A and X are as defined above.

The compounds of formula (Ib) are compounds of formula (I) in which $R_1$ and $R_2$ form, with the phenyl ring to which they are attached, a coumarin ring and $R_3$, $R_4$ and $R_6$ are each a hydrogen atom.

Preferably, in the compounds of formula (Ib) of the invention, $R_5$ is a hydrogen atom, $R_7$ and $R_8$ each independently represent a hydrogen atom, a $C_1$-$C_6$ alkyl group, an aralkyl group, an aryl group or a carboxyalkyl group, or $R_7$ and $R_8$, together with the two carbon atoms to which they are attached, form a $C_4$-$C_6$ ring, A is an amino acid chosen from leucine, proline and alanine, and X is the t-butoxycarbonyl blocking agent or nothing.

According to yet another particular embodiment, the compounds of the invention are enzymatic substrates of formula (Ic):

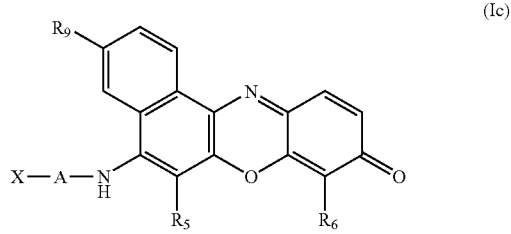

(Ic)

in which $R_5$, $R_6$, $R_9$, A and X are as defined above.

The compounds of formula (Ic) are compounds of formula (I) in which the radicals $R_3$ and $R_4$ form, with the phenyl ring to which they are attached, a naphthalene ring and $R_1$ and $R_2$ are each a hydrogen atom.

Preferably, in the compounds of formula (Ic), the groups $R_5$, $R_6$ and $R_9$ each represent a hydrogen atom, A is an amino acid chosen from leucine, proline and alanine, and X is the t-butoxycarbonyl blocking agent or nothing.

According to yet another embodiment, the compounds of the invention are enzymatic substrates of formula (Id):

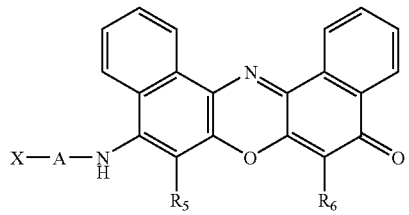

(Id)

in which $R_5$, $R_6$, A and X are as defined above.

The compounds of formula (Id) are compounds of formula (I) in which the radicals $R_1/R_2$ and $R_3/R_4$ each form, with the phenyl ring to which they are attached, a naphthalene ring.

The compounds of the invention can be prepared according to several methods of production depending on the ring that the radicals $R_1/R_2$ and $R_3/R_4$ form, whether $R_1/R_2$ form, with the phenyl ring to which they are attached, a naphthalene ring, or whether $R_1/R_2$ form, with the phenyl ring to which they are attached, a coumarin ring, or whether $R_3/R_4$ form, with the phenyl ring to which they are attached, a naphthalene ring, or whether $R_1/R_2$ and $R_3/R_4$ each form, with the phenyl ring to which they are attached, a naphthalene ring.

Thus, the compounds of formula (I) in which $R_1$ and $R_2$ form, with the phenyl ring to which they are attached, a naphthalene ring, can be prepared according to the procedure represented in scheme 1 below:

Scheme 1

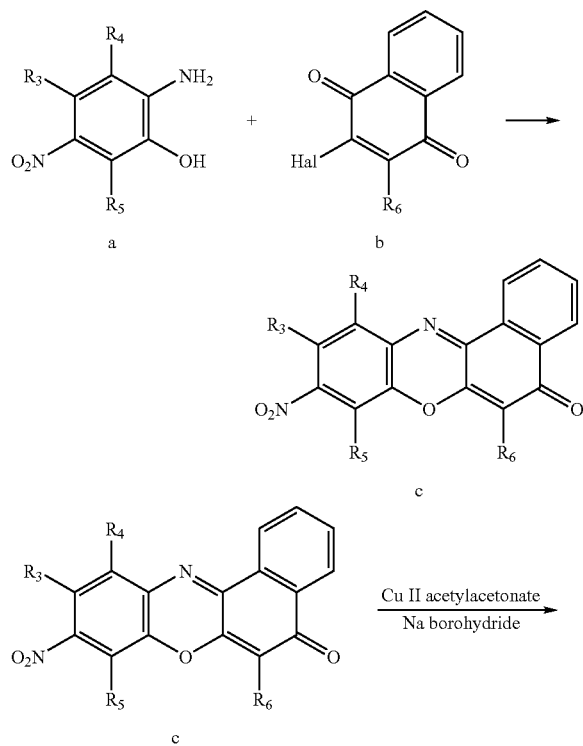

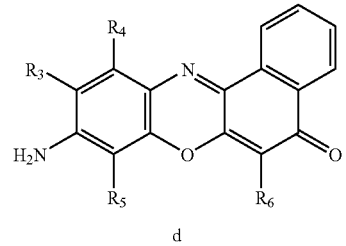

d

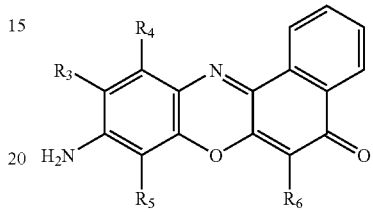

d  6

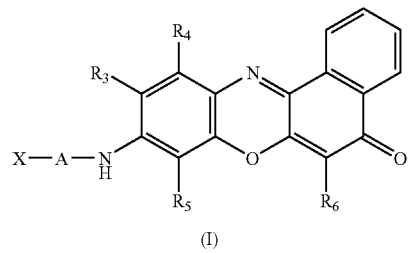

(I)

According to scheme 1 above, the compounds of formula (I) in which $R_1$ and $R_2$ form, with the phenyl ring to which they are attached, a naphthalene ring, are prepared by reaction of an appropriate 2-amino-5-nitrophenol compound (a) with appropriate halogenated 1,4-naphthoquinone (b), which has been heated beforehand to boiling point and then cooled to 25° C., so as to form the corresponding 9-nitro-benzo[a]phenoxazinone (c). This compound c is subsequently reacted with a mixture of copper II acetylacetonate that is reacted beforehand with sodium borohydride so as to form the compound (d). The compound (d) is subsequently reacted with one or more optionally protected amino acids (6) in a bath cooled to approximately −12° C., so as to give the compound of formula (I). It should be noted here that, of course, when A is a single amino acid, A' in the compound (6) corresponds to A of the compound (I), but comprising an additional hydroxyl group. In other words, when A is a single amino acid, A' ends with —C(O)OH, while A is linked to —NH— via —C(O)—, losing —OH. When A is a chain of at least two amino acids, the last amino acid of A' is as described above, i.e. it comprises, with respect to the last amino acid of A, an additional hydroxyl group.

The compounds of formula (Ia) in which $R_1$ and $R_2$ form, with the phenyl ring to which they are attached, a naphthalene ring, and $R_6$ is a hydrogen atom, can also be prepared according to the method described in scheme 1a hereinafter.

Scheme 1a

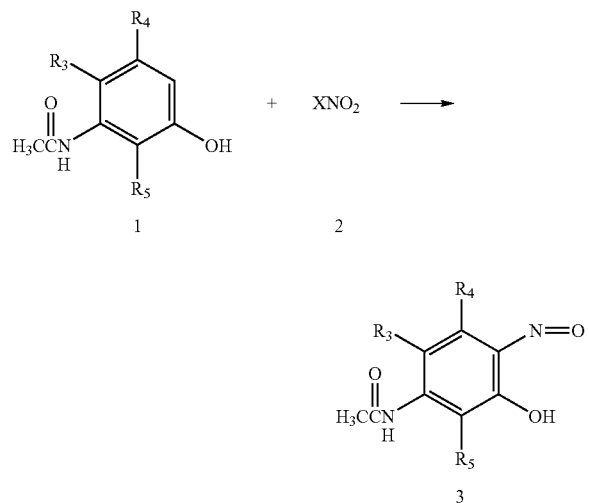

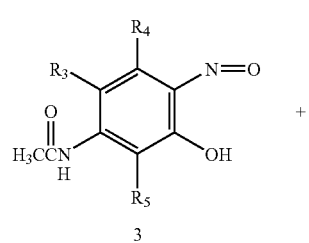

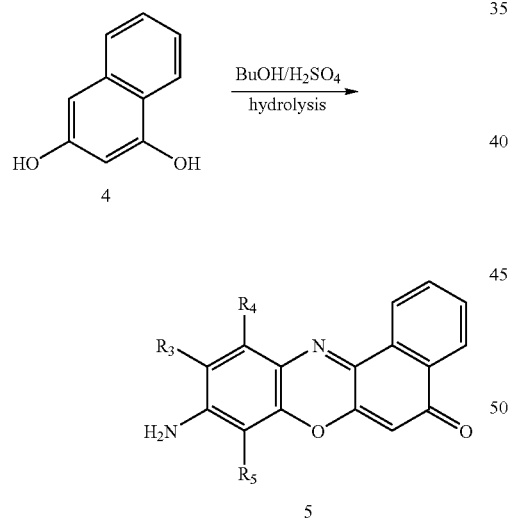

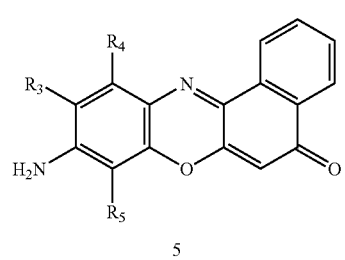

According to this scheme 1a, the compounds of formula (Ia) are prepared by reaction of an appropriate 3-acetamidophenol compound (1) with a nitrite (2), such as a sodium nitrite (X=Na), a potassium nitrite (X=K), etc., at a temperature of −3° C. The nitroso acetamidophenol (3) thus obtained is subsequently reacted with 1,3-dihydroxynaphthalene (4) in a solvent such as butanol, by heating to a temperature of approximately 70° C., then adding concentrated sulfuric acid and continuing the heating to 90° C., and then cooling, so as to form the appropriate 9-acetamido-benzo[a]phenoxazin-5-one. The latter compound is subsequently hydrolyzed by heating with moderately concentrated sulfuric acid so as to give the 9-amino-benzo[a]phenoxazin-5-one (5). The last step is equivalent to that of scheme 1.

The compounds of formula (I) in which $R_1$ and $R_2$ form, with the phenyl ring to which they are attached, a coumarin ring, can be prepared according to the procedure represented in scheme 2 hereinafter:

Scheme 2

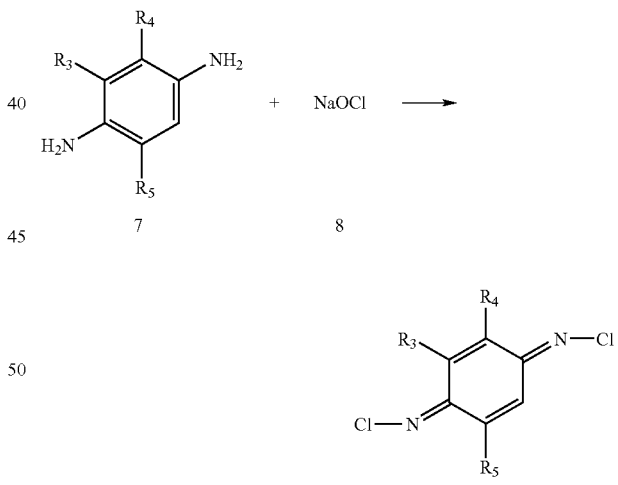

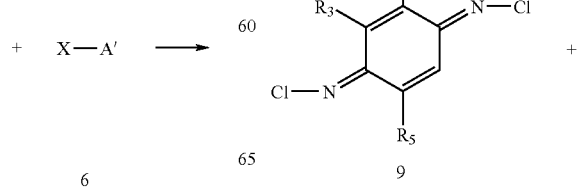

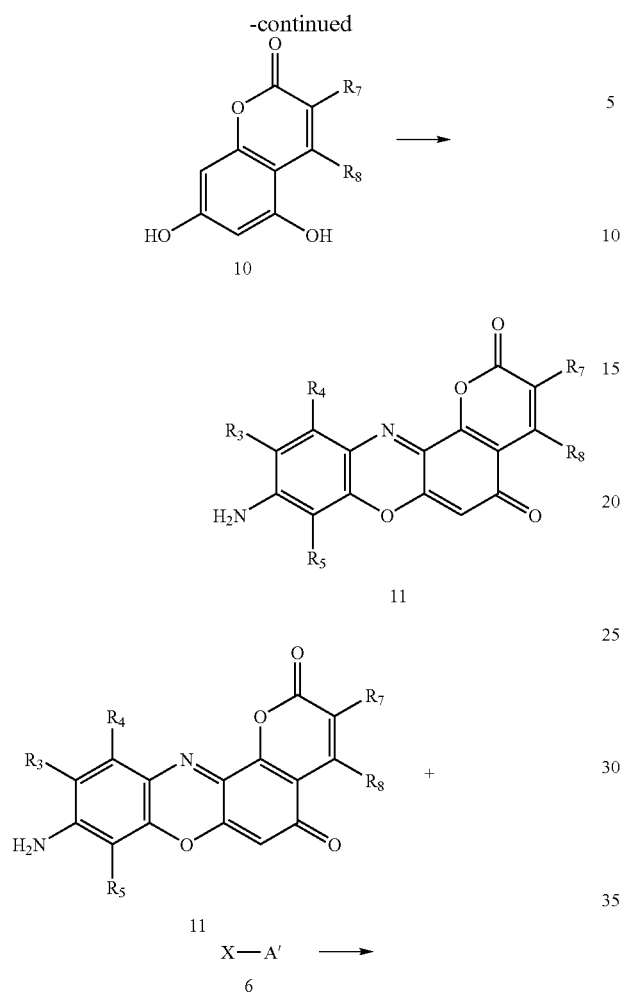

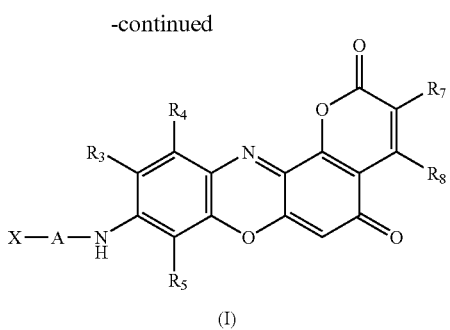

According to scheme 2 above, the compounds of formula (I) in which $R_1$ and $R_2$ form, with the phenyl ring to which they are attached, a coumarin ring, but also in which, as indicated in the general definition of the compounds of formula (I), $R_6$ is a hydrogen atom, are prepared by oxidizing and chlorinating the appropriate p-phenylenediamine derivative (7) in the presence of the compound (8) so as to obtain N,N'-dichloro-p-benzoquinonediimine (9) according to the method of Willstaetter and Mayer (1904, Chem. Ber., 37:1498). The latter compound is subsequently reacted in an alcoholic solution with 5,7-dihydroxycoumarin (10) so as to obtain the appropriate 7-amino-1,2-pyronylphenoxazin-3-one (11). The last step is equivalent to that of scheme 1.

The compounds of formula (Ib), which are compounds of formula (I) in which $R_1$ and $R_2$ form, with the phenyl ring to which they are attached, a coumarin ring, can of course be prepared with the method above.

The compounds of formula (I) in which $R_3$ and $R_4$ form, with the phenyl ring to which they are attached, a naphthalene ring, can be prepared according to the procedure represented in scheme 3 below:

Scheme 3

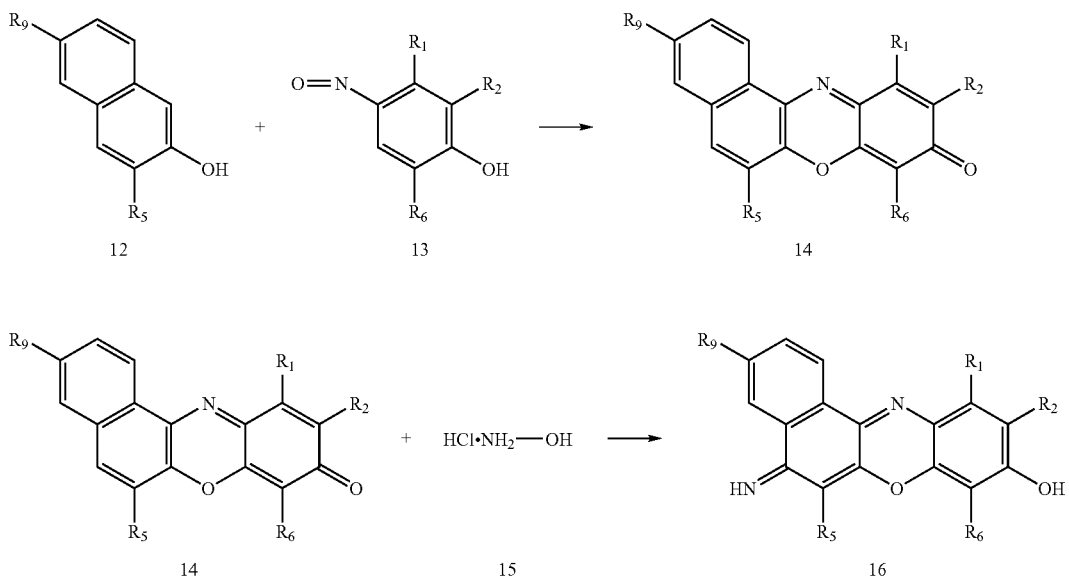

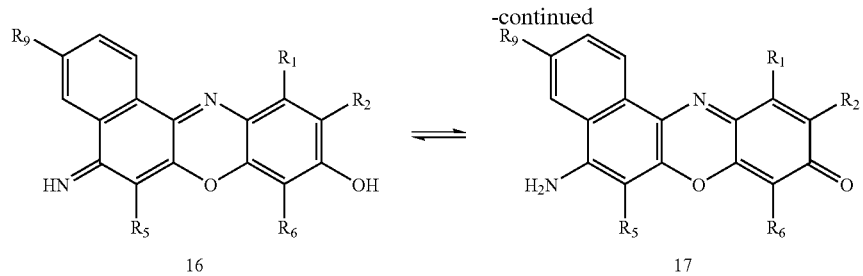

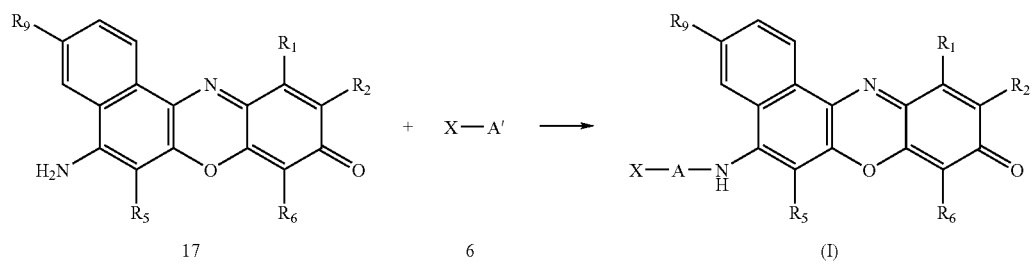

According to scheme 3 above, the compounds of formula (I) in which $R_3$ and $R_4$ form, with the phenyl ring to which they are attached, a naphthalene ring, can be prepared by condensation of appropriate 2-naphthol (12) with appropriate 4-nitrophenol (13) according to the method of Fischer & Hepp (reference 36.2, 1807, 1903) so as to give the appropriate naphthophenoxazone (14). The latter compound (14) is subsequently reacted with hydroxylamine hydrochloride (15) according to the method of Kehrman & Gottrau (reference 38, 2574, 1905) so as to obtain the hydroxyimine and aminoketone forms (compounds 16 and 17, respectively). The last step is equivalent to that of scheme 1.

The compounds of formula (Ic), which are compounds of formula (I) in which $R_3$ and $R_4$ form, with the phenyl ring to which they are attached, a naphthalene ring, can of course be prepared with the method above.

Finally, the compounds of the invention of formula (I) in which the radicals $R_1/R_2$ and $R_3/R_4$ each form, with the phenyl ring to which they are attached, a naphthalene ring (compounds of formula (Id)), can be prepared according to the procedure represented in scheme 4 below:

Scheme 4

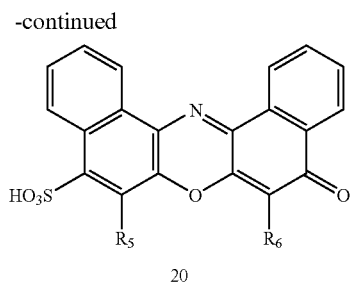

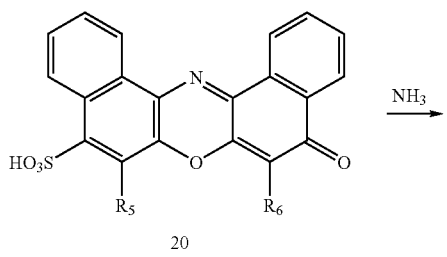

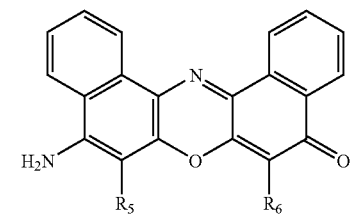

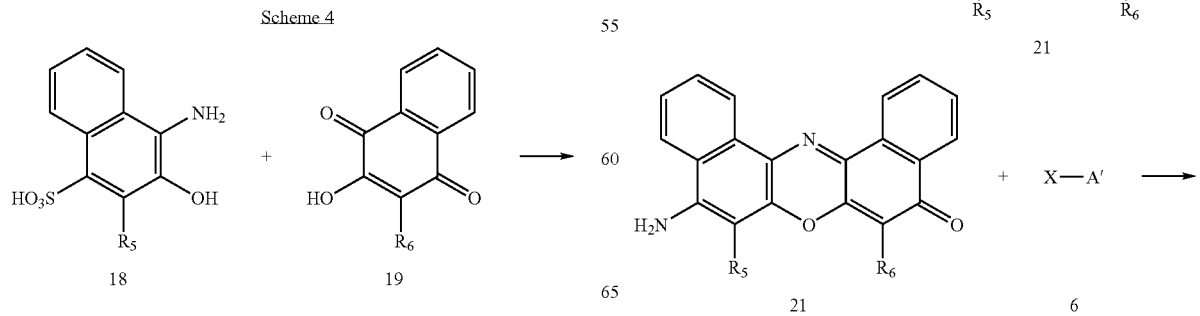

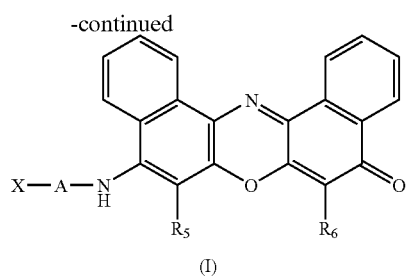

According to scheme 4 above, the compounds of formula (I) in which the radicals $R_1/R_2$ and $R_3/R_4$ each form, with the phenyl ring to which they are attached, a naphthalene ring, can be prepared by condensation of appropriate 1-amino-2-naphthol-4-sulfonic acid (18) with appropriate 2-hydroxy-1,4-naphthoquinone (19) so as to produce the appropriate dinaphthoxazonesulfonic acid (20). This compound (20) is subsequently heated in the presence of ammonium so as to produce the aminodinaphthoxazone (21). The last step of this procedure is equivalent to that of scheme 1.

In the above procedures, the starting reactants (compounds (1), (2), (4), (6), (7), (8), (10), (12), (13), (15), (18) and (19)) are commercially available, in particular from Aldrich.

A subject of the invention is also a reaction medium that uses at least one chromogenic enzymatic substrate of formula (I) as defined above, alone or in combination with at least one other enzymatic substrate specific for an enzymatic activity different from that detected by the substrate according to the invention.

In fact, when microorganisms expressing peptidase activity are seeded into or onto a reaction medium containing the compounds of the invention, a coloration occurs that does not diffuse in or on the reaction medium, and is therefore concentrated in the colonies.

The term "reaction medium according to the invention" is intended to mean a medium that allows the development of at least one enzymatic activity of at least one microorganism.

This reaction medium can either serve only as visualizing medium, or as culture medium and visualizing medium. In the first case, the microorganisms are cultured before seeding and, in the second case, the reaction medium also constitutes the culture medium, which constitutes a particular embodiment of the invention.

The reaction medium may be solid, semi-solid or liquid. The term "solid medium" is intended to mean, for example, a gelled medium.

Agar is the traditional solid medium in microbiology for culturing microorganisms, but it is possible to use gelatin or agarose. A certain number of preparations are commercially available, such as, for example, Columbia agar, Trypcase soy agar, Mac Conkey agar, Sabouraud agar or, more generally, those described in the Handbook of Microbiological Media (CRC Press).

Preferably, when the reaction medium is also a culture medium, it is in gelled form.

The amount of agar in the reaction medium is from 2 to 40 g/l and preferably from 9 to 25 g/l.

The enzymatic substrates of the invention can be used within a broad pH range, in particular between pH 5.5 and 10.

The concentration of enzymatic substrate of the invention in the reaction medium is between 0.025 and 0.40 g/l, and it is advantageously 0.05 g/l. This is because, at this substrate concentration, better coloration contrast is obtained.

The reaction medium may comprise at least one other substrate specific for an enzymatic activity different from that detected by the substrate according to the invention. The enzymatic hydrolysis of the other substrate(s) generates a detectable signal that is different from the signal detected by the substrate of the invention, such as, for example, different colored or fluorescent products, so as to allow the demonstration such as the detection and/or the identification and/or the quantification of one or more microorganisms.

As other specific substrate, mention may be made of substrates of indoxyl type, such as 5-bromo-4-chloro-3-indoxyl-β-D-glucoside (Biosynth) or 5-bromo-6-chloro-3-indoxyl-β-D-galactoside (Biosynth), or any other substrate used in the detection of microorganisms.

The concentration of the other specific enzymatic substrate is generally between 0.01 and 2 g/l. Those skilled in the art will be able to readily determine such a concentration according to the substrate used.

The reaction medium can also comprise one or more elements in combination, such as amino acids, peptones, carbohydrates, nucleotides, minerals, vitamins, antibiotics, surfactants, buffers, phosphate salts, ammonium salts, sodium salts or metal salts. Examples of media are described in the applicant's patent applications EP 656 421 and WO 99/09 207.

The enzymatic substrates and reaction media of the invention are therefore useful in the diagnosis of microorganisms with peptidase activity.

Thus, a subject of the present invention is also the use of a chromogenic enzymatic substrate of formula (I), or of a reaction medium as defined above, for the detection and/or identification and/or quantification of microorganisms expressing at least one peptidase activity.

The invention also relates to a method for the detection and/or identification and/or quantification of microorganisms expressing at least one peptidase activity, characterized in that in consists in:
  providing a reaction medium, as defined above,
  seeding the medium with a biological sample to be tested, leaving to incubate, and
  revealing the presence of at least one peptidase activity alone or in combination with at least one other enzymatic activity different from this same peptidase activity.

The seeding and incubation steps are widely known to those skilled in the art.

For example, the incubation temperature is 37° C. As regards the incubation atmosphere, it can equally be anaerobic or aerobic. However, the incubation is preferably carried out under aerobic conditions since this improves the enzymatic activity.

The revelation is carried out with the naked eye by visualizing a change in coloration that does not diffuse in the reaction medium, and is therefore concentrated in the colonies.

By way of microorganisms which may be diagnosed by means of the enzymatic substrate of the invention, mention may be made of Gram-negative bacteria, Gram-positive bacteria and yeasts.

By way of Gram-negative bacteria, mention may be made of bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella* and *Legionella*.

By way of Gram-positive bacteria, mention may be made of bacteria of the following genera: *Enterococcus, Strepto-* coccus, *Staphylococcus, Bacillus, Listeria, Clostridium, Mycobacteria* and *Corynebacteria*.

Examples of yeasts comprise yeasts of the following genera: *Candida, Cryptococcus, Saccharomyces* and *Trichosporon*.

The biological samples to be analyzed are any clinical sample, such as a saliva, blood, urine or stool sample, or any other sample the analysis of which may aid a clinician in putting forward a diagnosis. The sample may also be a sample of a product derived from, or a base product of, the food and/or pharmaceutical industry, in which it is necessary to either guarantee the absence of pathogenic microorganisms, or to count a contaminating flora, or to detect specific microorganisms.

The chromogenic substrates of the invention, in which A is alanine, have the advantage that they make it possible to differentiate Gram-negative bacteria from Gram-positive bacteria.

Thus, another subject of the invention consists of a method for differentiating, among bacteria, between those belonging to Gram-positive microbes and those belonging to Gram-negative microbes, characterized in that consists in:
 providing a reaction medium, as defined above and in which the substituent A of the chromogenic substrate is alanine,
 seeding the medium with a biological sample to be tested, leaving to incubate, and
 revealing the presence of at least one coloration synonymous with the presence of a Gram-negative microbe or Gram-negative microbes.

As regards the chromogenic substrates in which A is proline, they have the advantage that they make it possible to differentiate the yeast of the species *Candida albicans* from those of the species *Candida tropicalis* and *Candida glabrata*.

Thus, another subject of the invention relates to a method for differentiating the yeast of the species *Candida albicans* from those of the species *Candida tropicalis* and *Candida glabrata*, characterized in that it consists in:
 providing a reaction medium, as defined above and in which the substituent A of the chromogenic substrate is proline,
 seeding the medium with a biological sample to be tested, leaving to incubate, and revealing the presence of at least one coloration synonymous with the presence of the yeast of the species *Candida albicans*.

The invention will be understood more clearly from the following examples given by way of nonlimiting illustration.

EXAMPLE 1

Synthesis of 9-aminobenzo[a]phenoxazin-5-one (Compound (5) with $R_3=R_4=R_5=H$)

1.1 Preparation of 2-nitroso-5-acetamidophenol 9 g of 3-acetamidophenol (Aldrich) were dissolved in an aqueous solution (100 ml) containing 2.8 g of sodium hydroxide. The solution was cooled to −3° C. using an ice-salt bath and 5 g of sodium nitrite in water (12 ml) were added.

A solution of phosphoric acid diluted with an equal amount of water (25 ml) was added, using a separating funnel, to the stirred solution. Such an addition was carried out at a rate such that the temperature was maintained at 0° C. or below this temperature. A red-brown precipitate then formed. After further vigorous stirring for one hour, the pH was determined so as to guarantee complete acidity (pH<2).

The thick suspension thus obtained was filtered and the residue was carefully washed with cold water so as to remove the excess acid and salts. After appropriate aspiration, the residue was dried in a vacuum desiccator. 7.36 g of 2-nitroso-5-acetamidophenol were obtained with a yield of 68.6%.

1.2 Preparation of 9-acetamidobenzo[a]phenoxazin-5-one 1.8 g of the crude product obtained in point 1.1 above and 1.60 g of 1,3-dihydroxynaphthalene (Aldrich) were dissolved in 50 ml of butan-1-ol while at the same time stirring and heating to 70° C. 1 g of concentrated sulfuric acid was added dropwise to the heated solution and the heating was continued to 90° C. After 30 min, the mixture was allowed to cool. The solid phase was removed by suction filtration and washing was performed with a little ethanol. After drying, the title compound was obtained with a yield of 76%.

The product obtained was subjected to thin layer chromatography on silica gel plates using ethyl acetate/toluene (3:1) as mobile phase. A light orange-yellow spot was obtained ($R_f$=0.8).

1.3 Preparation of 9-aminobenzo[a]phenoxazin-5-one 1.5 g of the compound obtained in point 1.2 above were dissolved in a minimal volume of sulfuric acid and water (1:1), while at the same time stirring and heating to 100° C. until a sample taken and diluted in water, and then extracted in ethyl acetate, no longer showed any starting product by thin layer chromatography. The dark solution thus obtained was stirred and was heated to boiling point for several minutes, and was then cooled and poured into an ice-water bath (300 ml). The precipitated base was finely divided, heating was then carried out to 40° C. and the product was left to stand overnight. The supernatant liquid was allowed to separate by settling out, and the suspension of product was filtered and washed with water. After drying, the intended product was obtained with a yield of 78%.

EXAMPLE 2

Aminoacylation of 9-aminobenzo[a]phenoxazin-5-one (Compound of Formula (I) in which $R_1/R_2$ Form a Naphthalene, $R_3=R_4=R_5=R_6=H$, A=an amino acid and X=N-t-BOC)

0.52 g (2 mmol) of the amino compound concerned, obtained in Example 1, was dissolved in 15 ml of dimethylformamide (high performance liquid chromatography quality) while at the same time heating, and then in 10 ml of tetrahydrofuran. This solution was hydrogenated in a three-necked flask using hydrogen (produced from sodium borohydrate/acetic acid), and also 0.1 g of 10% palladium-on-charcoal as catalyst. The dark violet color was replaced with a fluorescent green appearance. The hydrogenation was continued for 30 min, the flask was closed and was left to stand overnight.

3 mmol of amino acid protected with N-tBOC were dissolved in 10 ml of anhydrous THF and the product was cooled to −12° C. (ice/salt bath). 0.33 g (3.3 mmol) of N-methylmorpholine was added to the solution thus cooled, and then 0.42 g (3.1 mmol) of isobutyl chloroformate was added gently at between −12° C. and −9° C. After 5 min, the mixed anhydride reaction mixture above was poured into the stirred solution of reduced amine, the mixture was precooled to at least −5° C., while hydrogen was introduced so as to prevent reoxidation. After 10 min, the flask was closed and the content was stirred for a further 5 hours at ambient temperature.

The reaction mixture was filtered and the solvent (THF) was removed by rotary evaporation. The DMF solution was poured into a thoroughly stirred water-ice mixture and the precipitate was filtered off, washed with water and air-dried. The crude product was dissolved in dichloromethane (DCM) and was washed with dilute (0.2M) sodium hydroxide and then with water. After drying with magnesium sulfate, the solvent was eliminated.

In certain cases, the filtration of the DCM extract through a cone of silica gel removed the traces of the base material liable to be observed by thin layer chromatography.

The compound obtained in this example can then be deprotected in the following way: the product is dissolved in a small volume of ethyl acetate and stirred with an equal amount of ethyl acetate saturated with hydrogen chloride for 1 hour. An excess of anhydrous ether is added and the precipitated hydrochloride salt is rapidly filtered off, then washed with additional ether or ether/mineral essence, and then dried in vacuo.

EXAMPLE 3

Synthesis of
9-amino-6-carbethoxybenzo[a]phenoxazin-5-one (Compound of Formula I in which $R_1/R_2$ form a Naphthalene and $R_3=R_4=R_5=H$ and $R_6=-C(O)OR'$ with $R'=C_2H_5$)

3.1 Preparation of Ethyl 1,3-dihydroxynaphthoate

This compound was produced from diethyl malonate and phenylacetyl chloride according to the method of Meyer and Bloch (Org. Synth. Coll., Vol 3, p 132).

3.2 Preparation of 9-acetamido-6-carbethoxybenzo[a]phenoxazin-5-one 1.8 g (10 mmol) of 2-nitroso-5-acetamidophenol and 2.08 g (9 mmol) of ethyl 1,3-dihydroxynaphthoate were dissolved in 60 ml of butanol while heating and the mixture was stirred at 70° C. Concentrated sulfuric acid was gradually added dropwise and the solution was heated gradually to approximately 90° C. After 30 min, the reaction mixture was cooled and was kept at 5° C. overnight.

The red product was removed by suction filtration and washed with a little ethanol.

After drying, the 9-acetamido-6-carbethoxybenzo[a]phenoxazin-5-one was obtained with a yield of 65%.

3.3 Preparation of 9-amino-6-carbethoxybenzo[a]phenoxazin-5-one

The 9-acetamido-6-carbethoxybenzo[a]phenoxazin-5-one obtained in point 3.2 was dissolved in a mixture of sulfuric acid (3 ml) and ethanol (3 ml). The mixture was heated to 80° C. while at the same time gradually adding water (1 ml). The purple color characteristic of the amine rapidly appeared. The hydrolysis was continued until the sample, diluted with water, and then extracted in ethyl acetate, no longer showed any 9-acetamido-6-carbethoxybenzo[a]phenoxazin-5-one by thin layer chromatography.

The reaction mixture was poured into 150 ml of ice-cold water and the product was collected by suction filtration, and then washed with water and dried. The product was obtained with a yield of 85%.

EXAMPLE 4

Aminoacylation of
9-amino-6-carbethoxybenzo[a]phenoxazin-5-one

The procedure was carried out as described in Example 2, using the product obtained in Example 3 and using the appropriate amino acid, protected with N-t-Boc.

For the deprotection of the aminated compound, it was dissolved in 2 ml of trifluoroacetic acid, which operation was followed by precipitation from ether. The product was thus obtained in the form of an homogeneous orange powder by thin layer chromatography.

EXAMPLE 5

Synthesis of
9-amino-6-chlorobenzo[a]phenoxazin-5-one (Compound of Formula I in which $R_1/R_2$ form a Naphthalene and $R_3=R_4=R_5=H$ and $R_6=Cl$)

5.1 Preparation of 9-nitro-6-chlorobenzo[a]phenoxazin-5-one 1.54 g (10 mmol) of 95% pure 2-aminonitrophenol (Aldrich) were added to a suspension of 2.26 g (10 mmol) of 2,3-dichloro-1,4-naphthoquinone (Fluka) in ethanol, heated beforehand to boiling point, and then cooled to 25° C. The mixture was stirred and 1 g of anhydrous sodium acetate was added. After several hours, an orangey-brown precipitate formed. After continuous stirring for 24 h, the solid was isolated by suction filtration, dried and recrystallized from hot acetic acid (yield of 65%).

5.2 Preparation of 9-amino-6-chlorobenzo[a]phenoxazin-5-one 130 mg (1 mmol) of copper II acetylacetonate, suspended in 10 ml of ethanol, were stirred with 0.18 g (5 mmol) of sodium borohydride at ambient temperature until the formation of a brown compound derived from this catalysis (approximately 10 min). 1.29 g (4 mmol) of the compound obtained in point 5.1 above, in the form of a suspension in 10 ml of propan-1-ol, were added to this mixture, followed by 0.37 g (10 mmol) of sodium borohydride. The mixture was stirred for 3 h at 30° C.

After cooling, the reaction mixture was poured into an ice/water mixture, and the crude product was then recovered by filtration and was dried. It was purified by dissolving in hot butan-1-ol and by filtration in order to remove the products containing copper. After concentration, the title compound was crystallized so as to give 0.68 g of product.

EXAMPLE 6

Aminoacylation of
9-amino-6-chlorobenzo[a]phenoxazin-5-one

The procedure was carried out as described in Example 2, using the product obtained in Example 5 and using the appropriate amino acid, protected with N-t-Boc.

For the deprotection of the aminated compound, the procedure was also carried out as described in Example 2.

EXAMPLE 7

Synthesis of 5-aminobenzo[a]phenoxazin-9-one (Compound of formula I in which $R_3/R_4$ Form a Naphthalene and $R_1=R_2=R_5=R_6=R_9=H$)

7.1 Preparation of Naphthophenoxazone

The method of Fisher & Hepp (above) was used without significant modification, carrying out the condensation of 4-nitrosophenol and of 2-naphthol in glacial acetic acid using zinc chloride as condensation agent.

The crude product was recrystallized from hot toluene/mineral essence with a yield of 25%.

The 4-nitrosophenol used here is a commercial product obtained from Fluka that was converted in the following way: this product was purified by dissolving it in ether, by filtering it through a Phase-Sep paper and by stirring with Norite for one hour. After filtration, the ethereal solution was rotary-evaporated so as to obtain a small volume and cooled so as to obtain a crystalline product of pure nitrosophenol.

7.2 Preparation of the Amine Product

According to the method of Kehrmann & Gottrau (above), 3.0 g of the naphthophenoxazone obtained in point 7.1 above and 3.0 g of hydroxylamine hydrochloride were mixed with 200 ml of absolute ethanol and the mixture was gradually heated to boiling point. The red color of the naphthophenoxazone was gradually replaced with an orange color and precipitation of the hydrochloride of the base occurred. The precipitate was removed by filtration, washed with a little ethanol, and then dried so as to obtain the hydrochloride with a yield of 63%.

1 g of the salt thus obtained was decomposed by heating with water, and then by cooling so as to give a green residue of the free base. The product was filtered and dissolved in a few ml of ethanol at 40° C. while at the same time adding a sufficient amount of HCl for solution. The fluorescent violet-red solution was heated with a sufficient amount of anhydrous sodium acetate to give the free base (dark green metal needles). The product was filtered, washed with hot water, and dried to attain a yield of 97%.

EXAMPLE 8

Synthesis of 7-amino-1,2-(3',4'-cyclopenteno-2'-pyronyl)-phenoxazin-3-one (Compound of Formula I in which $R_1/R_2$ Form a Coumarin, $R_7$ and $R_9$, Together with the Two Carbon Atoms to which they are Attached, Form a Cyclopentene and $R_3=R_4=R_5=R_6=H$)

8.1 Preparation of 5,7-dihydroxy-3,4-cyclopentenocoumarin 3.02 g (24 mmol) of phloroglucinol and 3.12 g (20 mmol) of ethyl 2-oxocyclopentanecarboxylate were mixed together in a small flask using a little ethanol. After cooling, 30 ml of a mixture of sulfuric acid/water at 75% mass by mass were added to the stirred mixture. The stirring was continued at ambient temperature for 48 h. The semi-solid product was poured into a thoroughly stirred ice/water mixture and filtration was carried out. The residue was thoroughly washed with water, drained by suction and air-dried.

Recrystallization from ethanol gave a product that was homogeneous by thin layer chromatography. The yield was 2.8 g.

8.2 Preparation of the Title Compound 2.18 g (10 mmol) of the 5,7-dihydroxy-3,4-cyclopentenocoumarin obtained in point 8.1 above were dissolved in 40 ml of hot ethanol and 1.74 g (10 mmol) of 1,4-dichloro-p-benzoquinonediimine were added to the stirred solution. The reaction mixture was slowly brought to reflux above a water-bath for several minutes, during which time the liquid became deep violet in color. After refluxing for a further 20 min, the reaction mixture was poured into 250 ml of an ice/water mixture containing 2 g of acetate. The colorant separated in the form of a dark blue precipitate. The precipitate thus obtained was removed by suction filtration and was washed with water. The dried product (1.5 g) could be recrystallized from acetic acid and butan-1-ol.

EXAMPLE 9

Synthesis of 7-amino-1,2-(4'-methyl-2'-pyronyl)phenoxazin-3-one (Compound of Formula I in which $R_1/R_2$ Form a Coumarin, $R_8$ is a Methyl and $R_7=R_3=R_4=R_5=R_6=H$)

9.1 Preparation of 5,7-dihydroxy-4-methylcoumarin

A mixture of 2.77 g (22 mmol) of phloroglucinol and 2.6 g (20 mmol) of ethyl acetoacetate were melted together, the mixture was cooled, and 40 ml of a mixture of sulfuric acid/water (75% w/w) was added rapidly to the semi-solid mass. The mixture was stirred for 24 h, during which time a semi-solid mass formed. It was poured into a mixture of ice/water (300 ml) containing 5 g of sodium acetate and the precipitate was recovered by suction filtration.

After repeated washing with water and drying, the crude product was recrystallized from hot ethanol so as to give 3.05 g of coumarin.

9.2 Preparation of 7-amino-1,2-(4'-methyl-2'-pyronyl)phenoxazin-3-one 1.92 g (10 mmol) of 5,7-dihydroxy-4-methylcoumarin were dissolved in 50 ml of anhydrous methanol. 7.5 g (0.125 mol) of urea were added to the stirred hot solution in order to moderate the exothermicity and to reduce the chlorination of the product. 1.74 g (10 mmol) of 1,4-dichlorobenzoquinonediimine were added to the reaction mixture, which had been refluxed for 2 h with stirring.

The dark purple solution was poured into a thoroughly stirred mixture of water/ice containing 10 g of sodium acetate. The dark purple precipitate was removed by vacuum filtration and drying was carried out. The crude product was purified by suspension in 200 ml of methanol heated to 50° C. while at the same time gradually adding to the thoroughly stirred mixture a solution of 5 g of sodium dithionite and 5 g of sodium carbonate in 20 ml of water. A yellowy-brown-colored precipitate formed.

The reaction mixture was rapidly filtered so as to isolate a precipitate of the colorant in the dihydro form. It was washed with a mixture of ice/water containing a little sodium dithionite and the precipitate thus made moist was transferred into 100 ml of methanol. The rapidly stirred solution was heated to 40° C. and water was gradually added, thereby making it possible to reoxidize the colorless colorant (in dihydro form) and to obtain a dark purplish-brown precipitate. Finally, 100 ml of water were added so as to end the oxidation and the precipitation of the colorant, which was dried after having been removed by filtration. Thin layer chromatography indicated only a single purple compound and a few traces of the same compound in the dihydro form.

EXAMPLE 10

Synthesis of 7-amino-1,2-(3'-carboxyethyl-4'-methyl-2'-pyronyl)phenoxazin-3-one (Compound of formula I in which $R_1/R_2$ Form a Coumarin, $R_7$=carboxyethyl, $R_8$=methyl and $R_3=R_4=R_5=R_6=H$)

10.1 Preparation of Ethyl 5,7-dihydroxy-4-methylcoumarin-3-propanoate 2.77 g (22 mmol) of phloroglucinol and 4.60 g (20 mmol) of diethyl acetylglutarate were mixed together, cooled, and stirred with 35 ml of a mixture of sulfuric acid/water at 75% mass/mass. The stirring was continued for 48 h. The product was isolated by pouring it into a stirred ice/water mixture and suction filtration was carried out. The residue was washed thoroughly with water and air-dried.

The product was converted directly to the free acid by suspending it in ethanol and stirring with an aqueous solution of potassium hydroxide (3 molar equivalents). After 4 h, the acid precipitated through the addition of 2M hydrochloric acid at pH 2. The abundant precipitate was removed by suction filtration, it was washed with water and it was drained off by suction. After air-drying, an amount of 3.8 g of the intended product was obtained.

10.2 Preparation of the Title Compound

This compound was prepared as in Example 8.1 using 1,4-dichloro-p-benzoquinonediimine and the acid obtained in point 10.1 above (equimolar amounts). The reaction mixture was poured into an ice/water mixture, adding hydrochloric acid until a pH of 2 was obtained in order to ensure complete precipitation of the free carboxylic acid form of the colorant. The amount of dried product obtained was 2.2 g.

EXAMPLE 11

Detection of Microorganisms Expressing Leucine-Peptidase Activity 11.1 Preparation of the Detection Media The detection medium was prepared by mixing 1.4 g of biogelytone (bioMérieux), 0.84 g of meat extract (bioMérieux), 2.24 g of NaCl (Merck), 280 µl of a solution of IPTG (isopropylthio-β-D-galactopyranoside, BIOSYNTH) in water (concentration 10 g/l) and 4.2 g of European agar (bioMérieux).

The substrate of the invention obtained in Example 2, in which the amino acid is leucine (leucine-9-aminobenzo[a]phenoxazin-5-one or Leu-ABP), or else a substrate of the prior art, which is leucine-aminomethylcoumarin (Leu-AMC, BACHEM), was then added in the following way: 280 ml of osmosed water were added to the medium, and the mixture was melted in a waterbath at 100° C. The mixture was autoclaved for 15 min at 121° C. and cooled to 50° C. in a waterbath.

The substrate solubilized in DMSO (Merck) was then added according to the concentrations indicated in Table 1 below:

TABLE 1

|  | Medium 1 | Medium 2 | Medium 3 | Medium 4 | Medium 5 | Medium 6 | Medium 7 |
| --- | --- | --- | --- | --- | --- | --- | --- |
| Leu-ABP |  | 0 mg/l | 25 mg/l | 50 mg/l | 100 mg/l | 200 mg/l | 400 mg/l |
| Leu-AMC | 50 mg/l |  |  |  |  |  |  |

The medium was then poured into Petri dishes.

11.2 Seeding of the Microorganism Strains

Ten microorganism strains derived from the Applicant's collection, suspended in physiological saline, were seeded in colonies on each of the media. The dishes were incubated at 37° C. for 48 hours. The colonies formed were examined visually after incubation for 24 and 48 hours. The coloration of these colonies, the diffusion, and also the intensity of this coloration were noted.

11.3 Results

The results were expressed as intensity of coloration using an arbitrary scale ranging from 0 to 4 as a basis and also as diffusion also using an arbitrary scale ranging from 0 to 4 as a basis. These results are given in Table 2 below, where $T^a$ corresponds to the incubation time, $C^b$ corresponds to the growth diameter in mm, $I^c$ corresponds to the intensity of coloration, $Co^d$ corresponds to the color of the colony and $D^e$ corresponds to the diffusion, B corresponds to fluorescent blue and R corresponds to pink.

TABLE 2

| Strain | $T^a$ | Medium 1 Activity | | | | Medium 2 Activity | | | | Medium 3 Activity | | | | Medium 4 Activity | | | |
| --- | --- | --- | --- | --- | --- | --- | --- | --- | --- | --- | --- | --- | --- | --- | --- | --- | --- |
|  |  | $C^b$ | $I^c$ | $Co^d$ | $D^e$ | $C^b$ | $I^c$ | $Co^d$ | $D^e$ | $C^b$ | $I^c$ | $Co^d$ | $D^e$ | $C^b$ | $I^c$ | $Co^d$ | $D^e$ |
| Escherichia | 24 h | 1.8 | 3 | B | 4 | 1.8 |  |  |  | 1.8 | 0.0 | R |  | 1.7 | 0.5 | R | 0.5 |
| coli | 48 h | 1.8 | 3 | B | 4 | 1.8 |  |  |  | 1.8 | 0.25 | R | 0.25 | 1.8 | 0.5 | R | 0.5 |
| Citrobacter | 24 h | 0.8 | 3 | B | 4 | 0.8 |  |  |  | 0.7 | 1.5 | R | 0.5 | 0.7 | 1.5 | R | 0.5 |
| freundii | 48 h | 1 | 3 | B | 4 | 0.8 |  |  |  | 0.7 | 2.5 | R | 0.5 | 0.7 | 2.5 | R | 0.75 |
| Klebsiella | 24 h | 1.8 | 3 | B | 4 | 1.8 |  |  |  | 1.8 | 1.5 | R | 0.25 | 1.7 | 1.5 | R | 0.5 |
| pneumoniae | 48 h | 1.8 | 3 | B | 4 | 1.8 |  |  |  | 1.8 | 2 | R | 0.25 | 1.7 | 2.5 | R | 0.75 |
| Enterobacter | 24 h | 0.8 | 3 | B | 4 | 0.7 |  |  |  | 0.7 | 1.5 | R | 0.5 | 0.5 | 2.5 | R | 0.5 |
| cloaccae | 48 h | 0.8 | 3 | B | 4 | 0.7 |  |  |  | 0.7 | 2.5 | R | 0.5 | 0.5 | 3 | R | 0.75 |
| Serratia | 24 h | 0.5 | 2 | B | 4 | 0.5 |  |  |  | 0.5 | 0.5 | R |  | 0.4 | 1 | R |  |
| marcescens | 48 h | 0.7 | 3 | B | 4 | 0.7 |  |  |  | 0.7 | 2.5 | R | 0.5 | 0.5 | 3 | R | 0.5 |
| Pseudomonas | 24 h | 2 | 1 | B | 4 | 2 |  |  |  | 2 |  |  |  | 2 | 0.75 | R |  |
| aeruginosa | 48 h | 2 | 3 | B | 4 | 2 |  |  |  | 2 | 1 | R | 0.5 | 2 | 2.5 | R | 1 |
| Staphylococcus | 24 h | 1.7 | 2.5 | B | 4 | 1.7 |  |  |  | 0.3 |  |  |  | 0.2 |  |  |  |
| aureus | 48 h | 1.7 | 3 | B | 4 | 1.7 |  |  |  | 0.7 | 0.25 | R | 0.25 | 0.2 |  |  |  |
| Enterococcus | 24 h | 0.4 | 0.5 | B | 4 | 0.4 |  |  |  | 0.3 | 0.0 | R | 0.25 | 0.3 | 0.0 | R | 0.25 |
| faecalis | 48 h | 0.4 | 1.5 | B | 4 | 0.4 |  |  |  | 0.3 | 0.0 | R | 0.25 | 0.3 | 0.0 | R | 0.25 |
| Candida | 24 h | 0.4 | 0.25 | B | 4 | 0.4 |  |  |  | 0.3 |  |  |  |  |  |  |  |
| albicans | 48 h | 0.5 | 1.5 | B | 4 | 0.7 |  |  |  | 0.5 | 0.25 | R |  | 0.3 |  |  |  |

TABLE 2-continued

| | Medium 5 | | | | Medium 6 | | | | Medium 7 | | | |
|---|---|---|---|---|---|---|---|---|---|---|---|---|
| | Activity | | | | Activity | | | | Activity | | | |
| Strain | $C^b$ | $I^c$ | $Co^d$ | $D^e$ | $C^b$ | $I^c$ | $Co^d$ | $D^e$ | $C^b$ | $I^c$ | $Co^d$ | $D^e$ |
| Escherichia coli | 1.8 | 0.0 | R | | 1.7 | | | | 1.8 | 0.75 | R | |
| | 1.8 | | R | | 1.7 | | | | 1.8 | | | |
| Citrobacter freundii | 0.7 | 0.75 | R | | 0.8 | 1 | R | | 0.7 | 2 | R | |
| | 0.7 | 1.5 | R | 0.25 | 0.8 | 2 | R | | 0.7 | 2 | R | |
| Klebsellia pneumoniae | 1.7 | 1.5 | R | | 1.7 | 2 | R | | 1.7 | 2.5 | R | |
| | 1.7 | 1.5 | R | 0.0 | 1.7 | 1 | R | | 1.8 | 1 | R | |
| Enterobacter cloaccae | 1 | 3 | R | | 1.5 | 3 | R | | 1.5 | 3 | R | |
| | 1.3 | 3 | R | 0.25 | 1.5 | 3 | R | | 1.7 | 3 | R | |
| Serratia marcescens | 0.4 | 0.25 | R | | 0.4 | | | | 0.4 | | | |
| | 0.5 | 1.5 | R | 0.0 | 0.5 | 1 | R | | 0.5 | 0.5 | R | |
| Pseudomonas aeruginosa | 2 | 0.75 | R | | 2 | 0.5 | R | | 2 | 0.5 | R | |
| | 2 | 2.5 | R | 0.5 | 2 | 2 | R | 0.3 | 2 | 0.5 | R | |
| Staphylococcus aureus | | | | | | | | | | | | |
| Enterococcus faecalis | 0.3 | | | | 0.3 | | | | 0.3 | | | |
| | 0.3 | 0.0 | R | 0.0 | 0.3 | | | | 0.3 | 0.5 | R | |
| Candida albicans | | | | | | | | | | | | |

The results indicated in Tables 1 and 2 above demonstrate that the chromogenic enzymatic substrates of the invention clearly make it possible to diagnose microorganisms expressing leucine-peptidase activity and that, compared with a substrate of the prior art, a very small amount of diffusion around the colony is observed.

EXAMPLE 12

Detection of Microorganisms Expressing Prolyl-Peptidase

12.1 Preparation of the Detection Media

The detection media were prepared by mixing 1.68 g of yeast extract (bioMérieux), 1.4 g of biocase (bioMérieux), 1.26 g of malt extract (bioMérieux), 0.08 g of glucose (Merck) and 3.92 g of agar (bioMérieux).

280 ml of osmosed water were added to the powder, and the mixture was then melted in a waterbath at 100° C. The product was separated into two flasks, each of 140 ml. Autoclaving was carried out at 121° C. for 15 min and the product was cooled to 50° C. in a waterbath.

L-Prolyl-7-amino-4-methylcoumarin (Pro-AMC, Bachem) was then added to the first flask as a control and L-prolyl-9-aminobenzo[a]phenoxazin-5-one (Pro-ABP, substrate of the invention obtained in Example 2, in which the amino acid is L-Proline) was then added to the second flask at the final concentration of 50 mg/l.

12.2 Seeding of the Microorganism Strains

Nine microorganism strains derived from the Applicant's collection, suspended in physiological saline, were seeded in colonies on each of the media. The dishes were incubated at 37° C. for 48 hours. The colonies formed were examined visually after incubation for 24 and 48 hours. The size of the colonies, their coloration and also the intensity of this coloration were noted.

12.3 Results

The results are expressed in Table 3 hereinafter, according to the rules and the nomenclature stated in paragraph 11.3.

TABLE 3

Prolyl-peptidase activity of microorganisms with the substrates Pro-AMC of the prior art and Pro-ABP of the invention

| | | Pro-AMC | | | Pro-ABP | | |
|---|---|---|---|---|---|---|---|
| | $T^a$ | $C^b$ | $I^c$ | $Co^d$ | $C^b$ | $I^c$ | $Co^d$ |
| Escherichia coli | 24 | 3 | 0.5 | B | 3 | 0.25 | R |
| | 48 | 3 | 0.5 | B | 3 | 3 | R |
| Klebsiella pneumoniae | 24 | 2.5 | 0.25 | B | 2 | | |
| | 48 | 3 | 0.25 | B | | | |
| Enterococcus faecalis | 24 | 0.8 | | | 0.7 | | |
| | 48 | 1.2 | | | 0.7 | | |
| Candida albicans | 24 | 1.2 | 2 | B | 0.8 | 2 | R |
| | 48 | 2.5 | 3 | B | 2.5 | 2 | R |
| Candida guilliermondii | 24 | 0.4 | | | 0.3 | | |
| | 48 | 1.8 | 3 | B | 1.8 | 2 | R |
| Candida glabrata | 24 | 0.3 | | | 0.4 | | |
| | 48 | 1.7 | | | 1.8 | | |
| Candida tropicalis | 24 | 1.2 | | | 1.2 | | |
| | 48 | 2 | | | 1.8 | | |
| Trichosporon beigelii | 24 | 0.7 | 0.25 | B | 0.5 | | |
| | 48 | 3 | 2 | B | 1.8 | 2 | R |
| Saccharomyces cerevisiae | 24 | 0.3 | | | 0.5 | | |
| | 48 | 1.7 | | | 2 | | |

The results indicated in the table above demonstrate that the chromogenic enzymatic substrates of the invention clearly make it possible to diagnose microorganisms expressing prolyl-peptidase activity, and in particular to separate yeast of the species Candida albicans from those of the species Candida tropicalis and Candida glabrata.

EXAMPLE 13

Detection of Microorganisms Expressing Alanyl-Peptidase Activity

13.1 Preparation of the Detection Media

The detection media were prepared by mixing 3.6 g of biogelytone (bioMérieux), 2.16 g of meat extract (bioMérieux), 1.26 g of malt extract (bioMérieux), 5.76 g of NaCl (Merck) and 10.8 g of agar (bioMérieux).

720 ml of osmosed water were added to the powder, and the mixture was then melted in a waterbath at 50° C. The product was separated into two flasks, each of 360 ml. Autoclaving was carried out at 121° C. for 15 min and the product was cooled to 100° C. in a waterbath.

L-Alanyl-7-amino-4-methylcoumarin (Ala-AMC, Bachem) was then added to the first flask as a control, at the final concentration of 50 mg/l, and L-alanyl-9-aminobenzo[a]phenoxazin-5-one (Ala-ABP, substrate of the invention obtained in Example 2, in which the amino acid is L-alanine), was then added to the second flask at the final concentration of 25 mg/l.

13.2 Seeding of the Microorganism Strains

Twenty-five microorganism strains derived from the Applicant's collection, suspended in physiological saline, were seeded in colonies on each of the media. The dishes were incubated at 37° C. for 48 hours. The colonies formed were examined visually after incubation for 24 and 48 hours. The size of the colonies, their coloration and also the intensity of this coloration were noted.

13.3 Results

The results are expressed in Table 4 hereinafter according to the rules and the nomenclature stated in paragraph 11.3.

TABLE 4

Alanyl-peptidase activity of microorganisms with the substrates Ala-AMC of the prior art and Ala-ABP of the invention

|  |  | Ala-AMC | | | Ala-ABP | | |
|---|---|---|---|---|---|---|---|
|  | $T^a$ | $C^b$ | $I^c$ | $Co^d$ | $C^b$ | $I^c$ | $Co^d$ |
| Acinetobacter baumanii | 24 | 1.5 | 3 | B | 1.7 | 3 | R |
|  | 48 | 1.5 | 3 | B | 1.7 | 3 | R |
| Salmonella typhimurium | 24 | 1.3 | 3 | B | 1 | 0.5 | R |
|  | 48 | 1.5 | 3 | B | 1.5 | 1 | R |
| Proteus mirabilis | 24 | 0.7 | 3 | B | 1.7 | 0.5 | R |
|  | 48 | 0.7 | 3 | B | 1.7 | 1.5 | R |
| Serratia liquefaciens | 24 | 0.7 | 3 | B | 0.7 | 3 | R |
|  | 48 | 1.3 | 3 | B | 1.3 | 3 | R |
| Serratia marcescens | 24 | 0.5 | 3 | B | 0.5 | 2 | R |
|  | 48 | 0.7 | 3 | B | 1 | 3 | R |
| Hafnia alvei | 24 | 0.7 | 3 | B | 0.5 | 0.5 | R |
|  | 48 | 0.7 | 3 | B | 0.5 | 1.5 | R |
| Edwardsiella tarda | 24 | 0.4 | 3 | B | 0.5 | 1 | R |
|  | 48 | 0.5 | 3 | B | 0.7 | 3 | R |
| Klebsiella pneumoniae | 24 | 1.2 | 3 | B | 1 | 3 | R |
|  | 48 | 1.8 | 3 | B | 1.5 | 3 | R |
| Escherichia coli | 24 | 1.7 | 3 | B | 1.7 | 1 | R |
|  | 48 | 1.7 | 3 | B | 1.8 | 1 | R |
| Pseudomonas aeruginosa | 24 | 0.3 |  |  | 0.3 | 1.7 | R |
|  | 48 | 0.5 | 2 | B | 0.5 | 3 | R |
| Enterobacter cloacae | 24 | 0.5 | 3 | B | 0.7 | 1.5 | R |
|  | 48 | 0.8 | 3 | B | 0.7 | 2 | R |
| Streptococcus pyogenes | 24 | 0.1 |  |  | 0.1 |  |  |
|  | 48 | 0.2 | 3 | B | 0.2 |  |  |
| Enterococcus faecium | 24 | 0.2 |  |  | 0.2 |  |  |
|  | 48 | 0.3 | 0.25 | B | 0.3 |  |  |
| Streptococcus agalactiae | 24 | 0.1 |  |  | 0.1 |  |  |
|  | 48 | 0.2 |  |  | 0.2 |  |  |
| Enterococcus faecalis | 24 | 0.3 |  |  | 0.3 |  |  |
|  | 48 | 0.4 |  |  | 0.3 |  |  |
| Staphylococcus epidermidis | 24 | 0.3 |  |  | 0.1 |  |  |
|  | 48 | 0.4 |  |  | 0.1 |  |  |
| Staphylococcus saprophyticus | 24 | 0.3 |  |  | 0.1 |  |  |
|  | 48 | 0.4 |  |  | 0.3 |  |  |
| Staphylococcus aureus | 24 | 0.5 |  |  | 0.1 |  |  |
|  | 48 | 0.7 |  |  | 0.3 |  |  |
| Bacillus subtilis | 24 | 1.7 |  |  | 0.1 |  |  |
|  | 48 | 1.8 |  |  | 0.5 |  |  |
| Corynebacterium | 24 | 0 |  |  | 0 |  |  |
| Pseudodiphteriticum | 48 | 0.4 | 2 | B | 0 |  |  |
| Listeria innocua | 24 | 0.2 |  |  | 0.2 |  |  |
|  | 48 | 0.3 |  |  | 0.3 |  |  |
| Saccharomyces cerevisiae | 24 | 0.1 |  |  | 0 |  |  |
|  | 48 | 0.2 |  |  | 0.2 |  |  |

TABLE 4-continued

Alanyl-peptidase activity of microorganisms with the substrates Ala-AMC of the prior art and Ala-ABP of the invention

|  |  | Ala-AMC | | | Ala-ABP | | |
|---|---|---|---|---|---|---|---|
|  | $T^a$ | $C^b$ | $I^c$ | $Co^d$ | $C^b$ | $I^c$ | $Co^d$ |
| Candida krusei | 24 | 0.7 |  |  | 0.5 |  |  |
|  | 48 | 1.5 | 0.25 |  | 1 |  |  |
| Candida glabrata | 24 | 0.2 |  |  | 0.1 |  |  |
|  | 48 | 0.3 |  |  | 0.3 |  |  |
| Candida albicans | 24 | 0.3 |  |  | 0.3 |  |  |
|  | 48 | 0.5 | 2 | B | 0.5 | 2 | R |

The results indicated in the table above demonstrate that the chromogenic enzymatic substrates of the invention clearly make it possible to diagnose microorganisms expressing alanyl-peptidase activity, and in particular to separate Gram-positive bacteria (not expressing the activity) from Gram-negative bacteria (expressing the activity).

EXAMPLE 14

Detection of Microorganisms Expressing β-Alanine Peptidase Activity 14.1 Preparation of the Detection Media 300 ml of Columbia medium were melted in a waterbath at 100° C. and autoclaved at 121° C. for 15 min. The product was then cooled to 50° C. in a waterbath.

This medium was separated into 3 flasks of 100 ml, and then, added at 50° C., as substrates, were those of Examples 4 and 6 for which the amino acid is β-alanine (respectively, β-alanine-9-amino-6-carbethoxybenzo[a]phenoxazin-5-one or β-Ala-ACAP and β-alanine-9-amino-6-chlorobenzo[a]phenoxazin-5-one or β-Ala-ACHP), solubilized in DMSO, according to the concentrations indicated in Table 5 below:

TABLE 5

|  | Medium 1 | Medium 2 | Medium 3 |
|---|---|---|---|
| β-Ala-ACAP |  | 60 mg/l |  |
| β-Ala-ACHP |  |  | 60 mg/l |

The medium was then poured into Petri dishes.

14.2 Seeding of the Microorganism Strains

Nine microorganism strains derived from the Applicant's collection, suspended in physiological saline, were seeded onto the media prepared in point 14.1 above according to a multipoint inoculation in a proportion of 100 000 cfu/spot. The dishes were incubated at 37° C. for 48 hours. The colonies formed (one colony per strain) were examined visually after incubation for 24 and 48 hours.

14.3 Results

The results are expressed in Table 6 hereinafter according to the rules and the nomenclature stated in paragraph 11.3 and where RP signifies pale pink.

TABLE 6

|  |  | Medium 1 | | | Medium 2 | | | Medium 3 | | |
|---|---|---|---|---|---|---|---|---|---|---|
|  | $T^a$ | $C^b$ | $I^c$ | $Co^d$ | $C^b$ | $I^c$ | $Co^d$ | $C^b$ | $I^c$ | $Co^d$ |
| Pseudomonas | 24 | 3 |  |  | 3 | 1 | R | 3 | 2 | R |
| aeruginosa 1 | 48 | 3 |  |  | 3 | 3 | R | 3 | 2 | RP |
| Pseudomonas | 24 | 3 |  |  | 3 | 2 | R | 2 | 2 | R |

TABLE 6-continued

| | T$^a$ | Medium 1 | | | Medium 2 | | | Medium 3 | | |
|---|---|---|---|---|---|---|---|---|---|---|
| | | C$^b$ | I$^c$ | Co$^d$ | C$^b$ | I$^c$ | Co$^d$ | C$^b$ | I$^c$ | Co$^d$ |
| aeruginosa 2 | 48 | 3 | | | 3 | 2 | R | 3 | 2 | RP |
| Pseudomonas | 24 | 1 | | | 1 | 2 | R | 1 | 2 | R |
| aeruginosa 3 | 48 | 2 | | | 2 | 3 | R | 2 | 2 | RP |
| Burkholderia cepacia 1 | 24 | 3 | | | 2 | | | 2 | | |
| | 48 | 3 | | | 2 | | | 2 | | |
| Burkholderia cepacia 2 | 24 | 3 | | | 2 | | | 2 | | |
| | 48 | 3 | | | 2 | | | 2 | | |
| Escherichia coli (NCTC 10418) | 24 | 3 | | | 2 | | | 2 | | |
| | 48 | 3 | | | 3 | | | 3 | | |
| Enterobacter cloacae (NCTC 11936) | 24 | 3 | | | 3 | | | 2 | | |
| | 48 | 3 | | | 3 | | | 3 | | |
| Enteroccus faecalis (NCTC 775) | 24 | 3 | | | 2 | | | 1 | | |
| | 48 | 3 | | | 2 | | | 1 | | |
| Candida albicans (NCTC) | 24 | 3 | | | 2 | | | 2 | | |
| | 48 | 3 | | | 2 | | | 2 | | |

The results indicated in the table above demonstrate that the chromogenic enzymatic substrates of the invention clearly make it possible to diagnose β-alanine peptidase activity specific for *P. aeruginosa* strains, all the other strains being negative for this enzymatic activity revealed by these substrates.

EXAMPLE 15

Detection of Microorganisms Expressing Alanine Peptidase Activity Using Substrates for A is at Least Two Amino Acids 15.1 Preparation of the Detection Media 1000 ml of Columbia medium was melted in a waterbath at 100° C. and autoclaved at 121° C. for 15 min. It was then cooled to 50° C. in a waterbath.

This medium was separated into 5 flasks of 200 ml, and then, added at 50° C., as substrates, was that of Example 2 for which A is:

- medium 1: L-alanine (L-alanine-9-aminobenzo[a]phenoxazin-5-one or A-ABP),
- medium 2: L-alanine-L-alanine (L-alanine-L-alanine-9-aminobenzo-[a]phenoxazin-5-one or AA-ABP),
- medium 3: L-alanine-L-alanine-L-alanine (L-alanine-L-alanine-L-alanine-9-aminobenzo[a]phenoxazin-5-one or AAA-ABP),
- medium 4: L-alanine-glycine (L-alanine-glycine-9-aminobenzo[a]phenoxazin-5-one or AG-ABP), and
- medium 5: glycine-L-alanine (glycine-L-alanine-9-aminobenzo[a]phenoxazin-5-one or GA-ABP), each substrate being solubilized in DMSO and used at a final concentration of 50 mg/l.

The medium was then poured into Petri dishes.

15.2 Seeding of the Microorganism Strains

Nine microorganism strains derived from the Applicant's collection, suspended in physiological saline, were seeded in colonies on the media prepared in point 15.1 above according to a multipoint inoculation in a proportion of 15 000 cfu/spot. The dishes were incubated at 37° C. for 48 hours. The colonies formed were examined visually after incubation for 24 and 48 hours.

15.3 Results

The results are expressed in Tables 7 and 8 hereinafter according to the rules and the nomenclature stated in paragraph 11.3 and where R=pink, RP=pale pink and I=colorless.

TABLE 7

| | T$^a$ | Medium 1 | | Medium 2 | | Medium 3 | |
|---|---|---|---|---|---|---|---|
| | | C$^b$ | Co$^b$ | C$^b$ | Co$^b$ | C$^b$ | Co$^b$ |
| Listeria monocytogenes (NCTC 11994) | 24 | 2 | I | 2 | R | 2 | R |
| | 48 | 2 | R | 2 | R | 2 | R |
| Micrococcus luteus (NCTC611) | 24 | 0 | | 0 | | 1 | R |
| | 48 | 0 | | 0 | | 3 | R |
| Staphylococcus aureus (NCTC 6571) | 24 | 0 | | 3 | I | 3 | I |
| | 48 | 2 | I | 2 | I | 3 | I |
| Staphylococcus epidermis (NCTC 11047) | 24 | 0 | | 2 | I | 2 | I |
| | 48 | 0 | | 2 | I | 2 | I |
| Acinetobacter baumannii (ATCC 19606) | 24 | 3 | R | 3 | R | 3 | R |
| | 48 | 3 | R | 3 | R | 3 | R |
| Enterobacter clocae (NCTC 11936) | 24 | 3 | R | 3 | R | 3 | R |
| | 48 | 3 | R | 3 | R | 3 | R |
| Escherichia coli (NCTC 10418) | 24 | 3 | R | 3 | R | 3 | R |
| | 48 | 3 | R | 3 | R | 3 | R |
| Pseudomonas aerigunosa (NCTC 10038) | 24 | 3 | R | 3 | R | 3 | R |
| | 48 | 3 | R | 3 | R | 3 | R |

TABLE 8

| | T$^a$ | Medium 1 | | Medium 4 | | Medium 5 | |
|---|---|---|---|---|---|---|---|
| | | C$^b$ | Co$^b$ | C$^b$ | Co$^b$ | C$^b$ | Co$^b$ |
| Listeria monocytogenes (NCTC 11994) | 24 | 2 | I | 2 | I | 2 | I |
| | 48 | 2 | R | 3 | I | 2 | R |
| Micrococcus luteus (NCTC 611) | 24 | 0 | | 1 | I | 0 | |
| | 48 | 0 | | 3 | R | 0 | |
| Staphylococcus aureus (NCTC 6571) | 24 | 0 | | 3 | I | 3 | I |
| | 48 | 2 | I | 3 | I | 3 | I |
| Staphylococcus epidermis (NCTC 11047) | 24 | 0 | | 3 | I | 1 | I |
| | 48 | 0 | | 3 | I | 2 | I |
| Acinetobacter baumannii (ATCC 19606) | 24 | 3 | R | 3 | RP | 3 | R |
| | 48 | 3 | R | 3 | R | 3 | R |
| Enterobacter clocae (NCTC 11936) | 24 | 3 | R | 3 | R | 3 | R |
| | 48 | 3 | R | 3 | R | 3 | R |
| Escherichia coli (NCTC 10418) | 24 | 3 | R | 3 | R | 3 | R |
| | 48 | 3 | R | 3 | R | 3 | R |
| Pseudomonas aerigunosa (NCTC 10038) | 24 | 3 | R | 3 | RP | 3 | RP |
| | 48 | 3 | R | 3 | R | 3 | R |

The results indicated in Tables 7 and 8 above demonstrate that, whatever the length of the amino acid chain of the chromogenic enzymatic substrates of the invention, the latter make it possible to detect the enzymatic expression of microorganism strains having alanine peptidase activity. In addition, due to the nature and the number of amino acids, it is possible to vary both the specificity and the sensitivity or the toxicity of the substrates for the diagnosis of said strains according to the strain under consideration.

EXAMPLE 16

Detection of Microorganisms by Combining a Substrate of the Invention and a Substrate of the Prior Art 16.1 Preparation of the Detection Medium 3.3 g of yeast extract, 2.75 g of Biocase, 2.475 g of malt extract, 0.165 g of glucose and 7.7 g of agar were mixed and 550 ml of osmosed water were added.

The mixture was melted in a waterbath at 100° C. and autoclaved at 121° C. for 15 min. It was then cooled to 50° C. in a waterbath.

The substrate of the invention prepared in Example 2, in which the amino acid is proline, was added in a proportion of 0.05 g/l and 5-bromo-4-chloro-3-indoxyl-β-D-glucoside was added, as other substrate of the prior art, in a proportion of 0.05 g/l.

The medium was then distributed into Petri dishes.

16.2 Seeding of the Microorganism Strains

Twelve microorganism strains derived from the Applicant's collection, suspended in physiological saline, were seeded in colonies on the medium prepared in point 16.1 above. The dishes were incubated at 37° C. for 48 hours. The colonies formed were examined visually after incubation for 24 and 48 hours.

16.3 Results

The results, indicated in Table 9 below, are expressed as growth with the size being indicated in mm, as activity and as color, $T^a$ representing the incubation time, R=pink, O=orange, V=green, T=turquoise, M=brown, GO=orangey-gray and GV=grayish-green.

TABLE 9

| Strain | $T^a$ | Growth | Activity | Color |
|---|---|---|---|---|
| Escherichia coli | 24 h | 3 | 2 | R |
| | 48 h | 3 | 3 | O |
| Serratia marcescens | 24 h | 1.5 | 2 | O |
| | 48 h | 1.7 | 2 | O |
| Serratia liquefaciens | 24 h | 1.5 | 2 | GV |
| | 48 h | 1.5 | 2 | M |
| Klebsellia pneumoniae | 24 h | 2 | 3 | GV |
| | 48 h | 3 | 3 | GO |
| Morganella morganii | 24 h | 2 | | |
| | 48 h | 2 | 2 | O |
| Acinetobacter baumanii | 24 h | 3 | 2 | R |
| | 48 h | 3 | 3 | R |
| Hafnia alvei | 24 h | 2 | 0.5 | R |
| | 48 h | 2.5 | 3 | R |
| Edwardsiella tarda | 24 h | 1.5 | 0 | O |
| | 48 h | 1.7 | 1.5 | R |
| Pseudomonas aeruginosa | 24 h | 1 | 2 | O |
| | 48 h | 1.5 | 3 | M |
| Listeria innocua | 24 h | 0.5 | 3 | T |
| | 48 h | 0.5 | 3 | T |
| Staphylococcus sciuri | 24 h | 0.5 | 3 | T |
| | 48 h | 0.5 | 3 | T |
| Enterococcus faecalis | 24 h | 1.2 | 3 | T |
| | 48 h | 1.2 | 3 | T |
| Candida albicans | 24 h | 1.2 | 2 | R |
| | 48 h | 1.5 | 3 | R |

The results indicated in Table 9 above show that a coloration characteristic of the enzymatic activities exhibited by the strains is clearly observed, as follows:
- a pink to orange coloration in the case of the strains having only the proline peptidase activity due to the hydrolysis of the substrate of the invention (*Escherichia coli, Morganella morganii, Acinetobacter baumanii, Hafnia alvei, Edwardsiella tarda* and *Candida albicans*),
- a turquoise coloration in the case of the strains having only the β-glucosidase activity due to the hydrolysis of the substrate of the prior art (*Staphylococcus sciuri, Enterococcus faecalis*) and
- a green to brown coloration, originating from the mixture of the 2 colorations pink/orange and turquoise, for the strains having the two enzymatic activities (*Serratia marcescens, Serratia liquefaciens, Klebsellia pneumoniae, Pseudomonas aeruginosa* and *Listeria innocua*).

Consequently, it is possible to detect several different enzymatic activities specific for each strain according to their metabolism.

The invention claimed is:

1. A method for at least one of the detection, identification and quantification of microorganisms expressing at least one peptidase activity, comprising incorporating a chromogenic enzymatic substrate corresponding to formula (I) below, within a reaction medium:

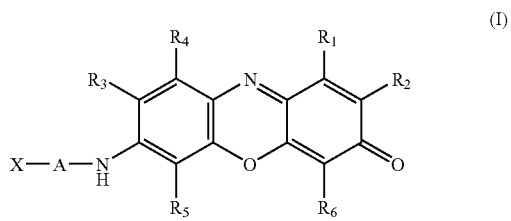

in which
$R_1$ and $R_2$ form, with the phenyl ring to which they are attached, a naphthalene ring of formula:

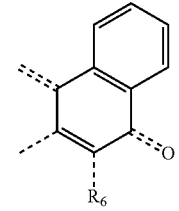

or an optionally substituted coumarin ring of formula:

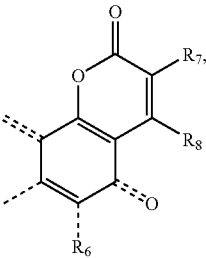

or $R_1$ and $R_2$ each independently represent a hydrogen atom, a $C_1$-$C_6$ alkyl group, a halogen atom, a —C(O)OR' group, a C(O)NR'R" group, an —SO$_3$H group or a sulfonamide group,
$R_3$ and $R_4$ form, with the phenyl ring to which they are attached, an optionally substituted naphthalene ring of formula:

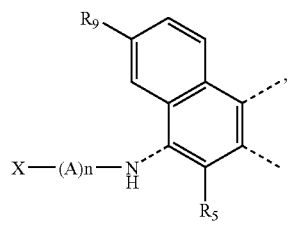

or $R_3$ and $R_4$ each independently represent a hydrogen atom, a halogen atom, a —C(O)OR' group, a C(O)NR'R" group, an —SO$_3$H group or a sulfonamide group, it being understood that:

(i) $R_1$ and $R_2$ and/or $R_3$ and $R_4$ form, with the phenyl ring to which they are attached, an optionally substituted naphthalene or coumarin ring as defined above, and (ii) when $R_1$ and $R_2$ form, with the phenyl ring to which they are attached, an optionally substituted coumarin ring, $R_3$ and $R_4$ do not form, with the phenyl ring to which they are attached, an optionally substituted naphthalene ring, $R_5$ and $R_6$ each independently represent a hydrogen atom, a halogen atom, a —C(O)OR' group, a C(O)NR'R" group, or a $C_1$-$C_6$ alkyl group, it being understood that $R_6$ represents a halogen atom when $R_1$ and $R_2$ and $R_3$ and $R_4$ each form, with the phenyl ring to which they are attached, a naphthalene ring, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or $R_7$ and $R_8$, together with the two carbon atoms to which they are attached, form a $C_4$-$C_6$ ring, $R_9$ represents a hydrogen atom, a bromine atom, a chlorine atom, a benzoyl group, a —CO$_2$H group or an —SO$_3$H group, it being understood that, when $R_9$ is different from a hydrogen atom, then $R_5$ is a hydrogen atom, R' represents a hydrogen atom or a $C_1$-$C_6$ alkyl group, R" represents a hydrogen atom or a $C_1$-$C_6$ alkyl group, or R' and R", together with the nitrogen atom to which they are attached, form a heterocyclic ring containing one or more hetero atoms, A represents at least one amino acid, and X represents a blocking agent or is not present.

2. A method for the detection and/or identification and/or quantification of microorganisms expressing at least one peptidase activity, comprising providing a reaction medium that incorporates a chromogenic enzymatic substrate corresponding to formula (I), below seeding the reaction medium with a biological sample to be tested, incubating the seeded reaction medium, and detecting whether at least one peptidase activity alone or in combination with at least one other enzymatic activity different from the peptidase activity is present;

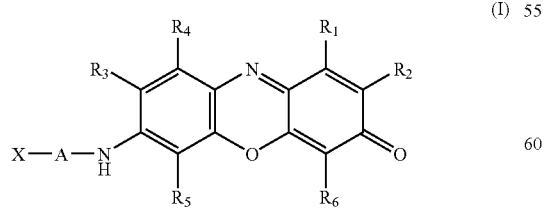

(I)

in which $R_1$ and $R_2$ form, with the phenyl ring to which they are attached, a naphthalene ring of formula:

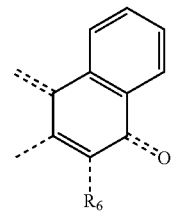

or an optionally substituted coumarin ring of formula:

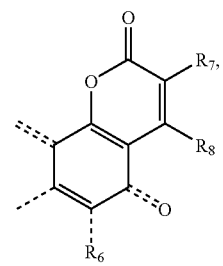

or $R_1$ and $R_2$ each independently represent a hydrogen atom, a $C_1$-$C_6$ alkyl group, a halogen atom, a —C(O)OR' group, a C(O)NR'R" group, an —SO$_3$H group or a sulfonamide group, $R_3$ and $R_4$ form, with the phenyl ring to which they are attached, an optionally substituted naphthalene ring of formula:

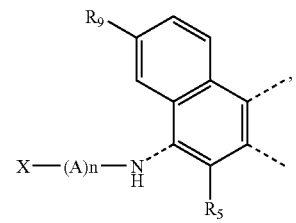

or $R_3$ and $R_4$ each independently represent a hydrogen atom, a halogen atom, a —C(O)OR' group, a C(O)NR'R" group, an —SO$_3$H group or a sulfonamide group, it being understood that:

(i) $R_1$ and $R_2$ and/or $R_3$ and $R_4$ form with the phenyl ring to which they are attached, an optionally substituted naphthalene or coumarin ring as defined above, and (ii) when $R_1$ and $R_2$ form, with the phenyl ring to which they are attached, an optionally substituted coumarin ring, $R_3$ and $R_4$ do not form, with the phenyl ring to which they are attached, an optionally substituted naphthalene ring, $R_5$ and $R_6$ each independently represent a hydrogen atom, a halogen atom, a —C(O)OR' group, a C(O)NR'R" group, or a $C_1$-$C_6$ alkyl group, it being understood that $R_6$ represents a halogen atom when $R_1$ and $R_2$ and $R_3$ and $R_4$ each form, with the phenyl ring to which they are attached, a naphthalene ring, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or $R_7$ and $R_8$, together with the two carbon atoms to which they are attached, form a $C_4$-$C_6$ ring, $R_9$ represents a hydrogen atom, a bromine atom, a chlorine atom, a benzoyl group, a —$CO_2H$ group or an —$SO_3H$ group, it being understood that, when $R_9$ is different from a hydrogen atom, then $R_5$ is a hydrogen atom, R' represents a hydrogen atom or a $C_1$-$C_6$ alkyl group, R" represents a hydrogen atom or a $C_1$-$C_6$ alkyl group, or R' and R", together with the nitrogen atom to which they are attached, form a heterocyclic ring containing one or more hetero atoms, A represents at least one amino acid, and X represents a blocking agent or is not present.

3. A method for differentiating, among bacteria, between those belonging to Gram-positive microbes and those belonging to Gram-negative microbes, comprising providing a reaction medium that incorporates a chromogenic enzymatic substrate corresponding to formula (I), below, seeding the reaction medium with a biological sample to be tested, incubating the seeded reaction medium, and detecting whether at least one coloration that is indicative of the presence of a Gram-negative microbe or a Gram-negative microbe is present;

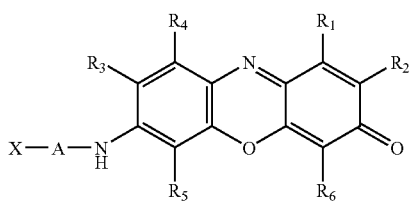

(I)

in which $R_1$ and $R_2$ form, with the phenyl ring to which they are attached, a naphthalene ring of formula:

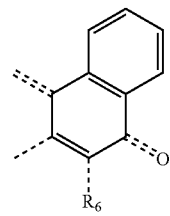

or an optionally substituted coumarin ring of formula:

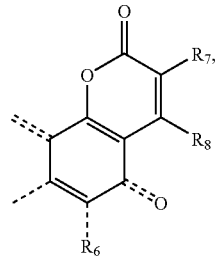

or $R_1$ and $R_2$ each independently represent a hydrogen atom, a $C_1$-$C_6$ alkyl group, a halogen atom, a —C(O)OR' group, a C(O)NR'R" group, an —$SO_3H$ group or a sulfonamide group, $R_3$ and $R_4$ form, with the phenyl ring to which they are attached, an optionally substituted naphthalene ring of formula:

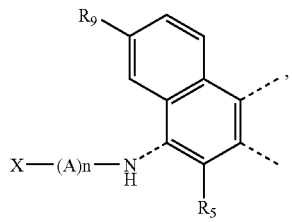

or $R_3$ and $R_4$ each independently represent a hydrogen atom, a halogen atom, a —C(O)OR' group, a C(O)NR'R" group, an —$SO_3H$ group or a sulfonamide group, it being understood that:

(i) $R_1$ and $R_2$ and/or $R_3$ and $R_4$ form, with the phenyl ring to which they are attached, an optionally substituted naphthalene or coumarin ring as defined above, and (ii) when $R_1$ and $R_2$ form, with the phenyl ring to which they are attached, an optionally substituted coumarin ring, $R_3$ and $R_4$ do not form, with the phenyl ring to which they are attached, an optionally substituted naphthalene ring, $R_5$ and $R_6$ each independently represent a hydrogen atom, a halogen atom, a —C(O)OR' group, a C(O)NR'R" group, or a $C_1$-$C_6$ alkyl group, it being understood that $R_6$ represents a halogen atom when $R_1$ and $R_2$ and $R_3$ and $R_4$ each form, with the phenyl ring to which they are attached, a naphthalene ring, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or $R_7$ and $R_8$, together with the two carbon atoms to which they are attached, form a $C_4$-$C_6$ ring, $R_9$ represents a hydrogen atom, a bromine atom, a chlorine atom, a benzoyl group, a —$CO_2H$ group or an —$SO_3H$ group, it being understood that, when $R_9$ is different from a hydrogen atom, then $R_5$ is a hydrogen atom, R' represents a hydrogen atom or a $C_1$-$C_6$ alkyl group, R" represents a hydrogen atom or a $C_1$-$C_6$ alkyl group, or R' and R", together with the nitrogen atom to which they are attached, form a heterocyclic ring containing one or more hetero atoms, A represents alanine, and X represents a blocking agent or is not present.

4. A method for differentiating a yeast of a species *Candida albicans* from those of a species *Candida tropicalis* and *Candida glabrata*, comprising providing a reaction medium that incorporates a chromogenic enzymatic substrate corresponding to formula (I), below, seeding the reaction medium with a biological sample to be tested, incubating the seeded reaction medium, and detecting whether at least one coloration that is indicative of the presence of yeast of the species *Candida albicans* is present;

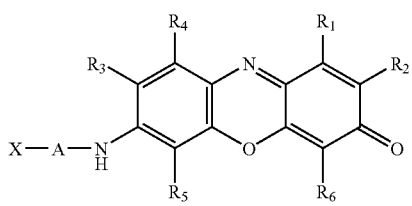

(I)

in which $R_1$ and $R_2$ form, with the phenyl ring to which they are attached, a naphthalene ring of formula:

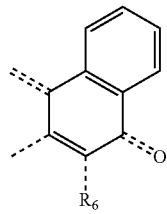

or an optionally substituted coumarin ring of formula:

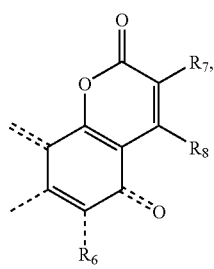

or $R_1$ and $R_2$ each independently represent a hydrogen atom, a $C_1$-$C_6$ alkyl group, a halogen atom, a —C(O)OR' group, a C(O)NR'R" group, an —SO$_3$H group or a sulfonamide group, $R_3$ and $R_4$ form, with the phenyl ring to which they are attached, an optionally substituted naphthalene ring of formula:

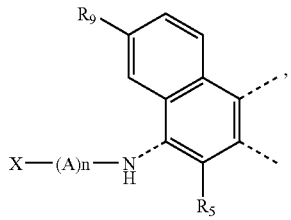

or $R_3$ and $R_4$ each independently represent a hydrogen atom, a halogen atom, a —C(O)OR' group, a C(O)NR'R" group, an —SO$_3$H group or a sulfonamide group, it being understood that:

(i) $R_1$ and $R_2$ and/or $R_3$ and $R_4$ form, with the phenyl ring to which they are attached, an optionally substituted naphthalene or coumarin ring as defined above, and (ii) when $R_1$ and $R_2$ form, with the phenyl ring to which they are attached, an optionally substituted coumarin ring, $R_3$ and $R_4$ do not form, with the phenyl ring to which they are attached, an optionally substituted naphthalene ring, $R_5$ and $R_6$ each independently represent a hydrogen atom, a halogen atom, a —C(O)OR' group, a C(O)NR'R" group, or a $C_1$-$C_6$ alkyl group, it being understood that $R_6$ represents a halogen atom when $R_1$ and $R_2$ and $R_3$ and $R_4$ each form, with the phenyl ring to which they are attached, a naphthalene ring, $R_7$ and $R_8$ each independently represent a hydrogen atom, a $C_1$-$C_6$ alkyl group, an aralkyl group, an aryl group, a carboxyalkyl group, a carboxyl group or a sulfonic acid group, or $R_7$ and $R_8$, together with the two carbon atoms to which they are attached, form a ring, $R_9$ represents a hydrogen atom, a bromine atom, a chlorine atom, a benzoyl group, a —CO$_2$H group or an —SO$_3$H group, it being understood that, when $R_9$ is different from a hydrogen atom, then $R_5$ is a hydrogen atom, R' represents a hydrogen atom or a $C_1$-$C_6$ alkyl group, R" represents a hydrogen atom or a $C_1$-$C_6$ alkyl group, or R' and R", together with the nitrogen atom to which they are attached, form a heterocyclic ring containing one or more hetero atoms, A represents proline, and X represents a blocking agent or is not present.

5. A method according to claim 1, wherein there is one and only one among $R_1$ and $R_2$ and $R_3$ and $R_4$ that forms, with the phenyl ring to which they are attached, an optionally substituted naphthalene or coumarin ring.

6. A method according to claim 1, wherein the chromogenic enzymatic substrate is of formula (Ia) below:

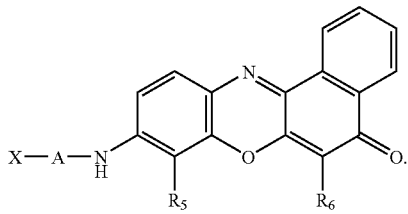

(Ia)

7. A method according to claim 6, wherein $R_5$ represents a hydrogen atom, $R_6$ represents a hydrogen atom or a halogen atom, A is an amino acid selected from the group consisting of leucine, proline and alanine, and X is a t-butoxycarbonyl blocking agent or is not present.

8. A method according to claim 1, wherein the chromogenic enzymatic substrate is of formula (Ib) below:

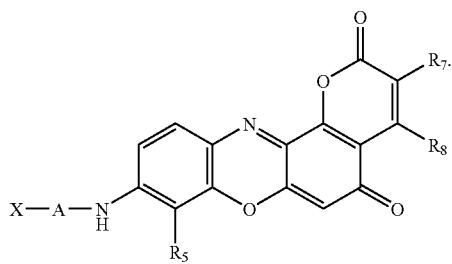

(Ib)

9. A method according to claim 8, wherein $R_5$ is a hydrogen atom, $R_7$ and $R_8$ each independently represent a hydrogen atom, a $C_1$-$C_6$ alkyl group, an aralkyl group, an aryl group or a carboxyalkyl group, or $R_7$ and $R_8$, together with the two carbon atoms to which they are attached, form a $C_4$-$C_6$ ring, A is an amino acid selected from the group consisting of leucine, proline and alanine, and X is a t-butoxycarbonyl blocking agent or is not present.

10. A method according to claim 1, wherein the chromogenic enzymatic substrate is of formula (Ic) below:

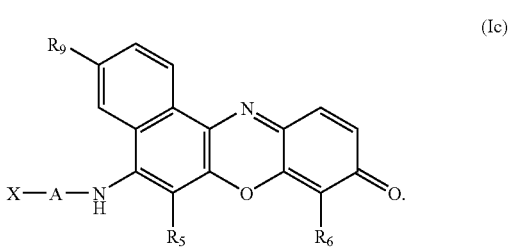

(Ic)

11. A method according to claim 10, wherein $R_5$, $R_6$ and $R_9$ each represent a hydrogen atom, A is an amino acid selected from the group consisting of leucine, proline and alanine and X is a t-butoxycarbonyl blocking agent or is not present.

12. A method according to claim 1, wherein the chromogenic enzymatic substrate is of formula (Id) below:

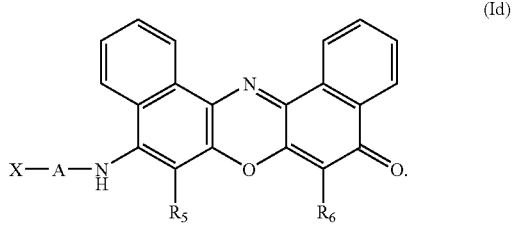

(Id)

* * * * *